US007606615B2

(12) United States Patent
Makower et al.

(10) Patent No.: US 7,606,615 B2
(45) Date of Patent: *Oct. 20, 2009

(54) METHODS AND APPARATUS FOR ACUTE OR CHRONIC DELIVERY OF SUBSTANCES OR APPARATUS TO EXTRAVASCULAR TREATMENT SITES

(75) Inventors: Joshua Makower, Los Altos, CA (US); Theodore C. Lamson, Pleasanton, CA (US); J. Christopher Flaherty, Topsfield, MA (US); John A. Reggie, Palo Alto, CA (US); John Y. Chang, Mountain View, CA (US); Joseph Catanese, III, Redwood City, CA (US); David R. Tholfsen, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1023 days.

This patent is subject to a terminal disclaimer.

(21) Appl. No.: 10/458,153

(22) Filed: Jun. 10, 2003

(65) Prior Publication Data

US 2005/0090748 A1  Apr. 28, 2005

Related U.S. Application Data

(63) Continuation of application No. 09/766,502, filed on Jan. 17, 2001, now Pat. No. 6,602,241.

(51) Int. Cl.
*A61M 25/00* (2006.01)
(52) U.S. Cl. .................. 600/435; 600/407; 600/431; 600/433
(58) Field of Classification Search .............. 600/407, 600/424, 431, 433, 435; 604/19–21
See application file for complete search history.

(56) References Cited

U.S. PATENT DOCUMENTS

| 4,530,698 | A | * | 7/1985 | Goldstein et al. | ............ 604/271 |
| 4,552,554 | A | * | 11/1985 | Gould et al. | ................. 604/104 |
| 4,772,264 | A | * | 9/1988 | Cragg | .......................... 604/158 |
| 5,085,631 | A | * | 2/1992 | Leighton | ....................... 604/28 |

(Continued)

FOREIGN PATENT DOCUMENTS

WO    WO 99/48545    9/1999

*Primary Examiner*—Brian Casler
*Assistant Examiner*—Peter Luong

(57) ABSTRACT

Methods and apparatus for delivery of substances or apparatus to target sites located outside blood vessels within the body of a human or animal patient. A vessel wall penetrating catheter is inserted into the vasculature, positioned and oriented within a blood vessel near the target extravascular site and a penetrator is advanced from the catheter so as to penetrate outwardly through the wall of the blood vessel in the direction of the target site. Thereafter, a delivery catheter is passed through a lumen of the penetrator to the target site. A desired substance or apparatus is then delivered to or obtained from the target site. In some applications, the penetrator may be retracted into the vessel wall penetrating catheter and the vessel wall penetrating catheter may be removed, leaving the delivery catheter in place for chronic or continuous delivery of substance(s) to and/or obtaining of information or samples from the target site. Alternatively, a delivery catheter having an occlusion member or balloon may be advanced into a vein or venule and the occlusion member or balloon may be used to occlude the lumen of the vein or venule during and after injection of a substance through the catheter, such that the substance will not be carried away by normal venous blood flow and will remain in the vein or venule for a sufficient period of time to have its intended effect (e.g. to enter adjacent tissues through capillary beds drained by that vein or venule).

65 Claims, 9 Drawing Sheets

U.S. PATENT DOCUMENTS

Figure 1:
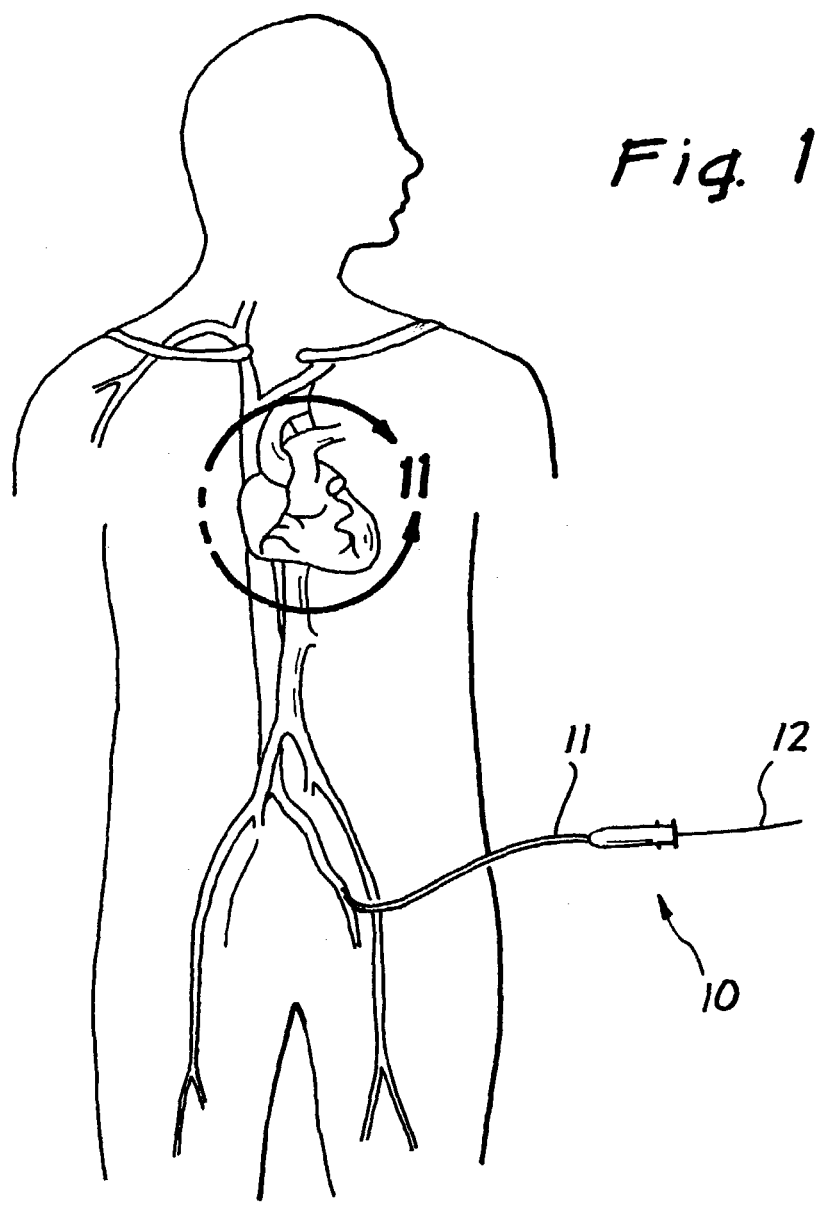
Figure 10A:
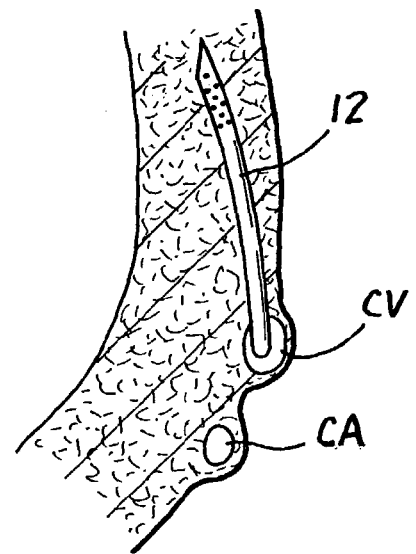

| | | | |
|---|---|---|---|
| 5,366,490 A | 11/1994 | Edwards et al. | |
| 5,762,630 A * | 6/1998 | Bley et al. | 600/585 |
| 5,993,427 A * | 11/1999 | Rolland et al. | 604/271 |
| 6,190,353 B1 * | 2/2001 | Makower et al. | 600/137 |
| 6,375,615 B1 * | 4/2002 | Flaherty et al. | 600/439 |
| 6,602,241 B2 * | 8/2003 | Makower et al. | 604/509 |
| 6,660,024 B1 * | 12/2003 | Flaherty et al. | 600/439 |
| 2002/0052576 A1 * | 5/2002 | Massengale | |
| 2002/0077594 A1 * | 6/2002 | Chien et al. | |
| 2002/0091352 A1 * | 7/2002 | McGuckin, Jr. et al. | |

* cited by examiner

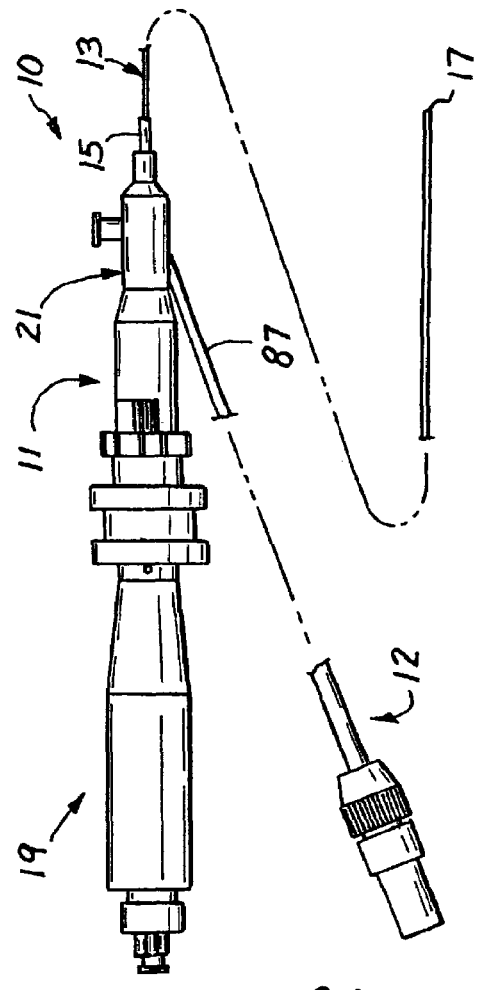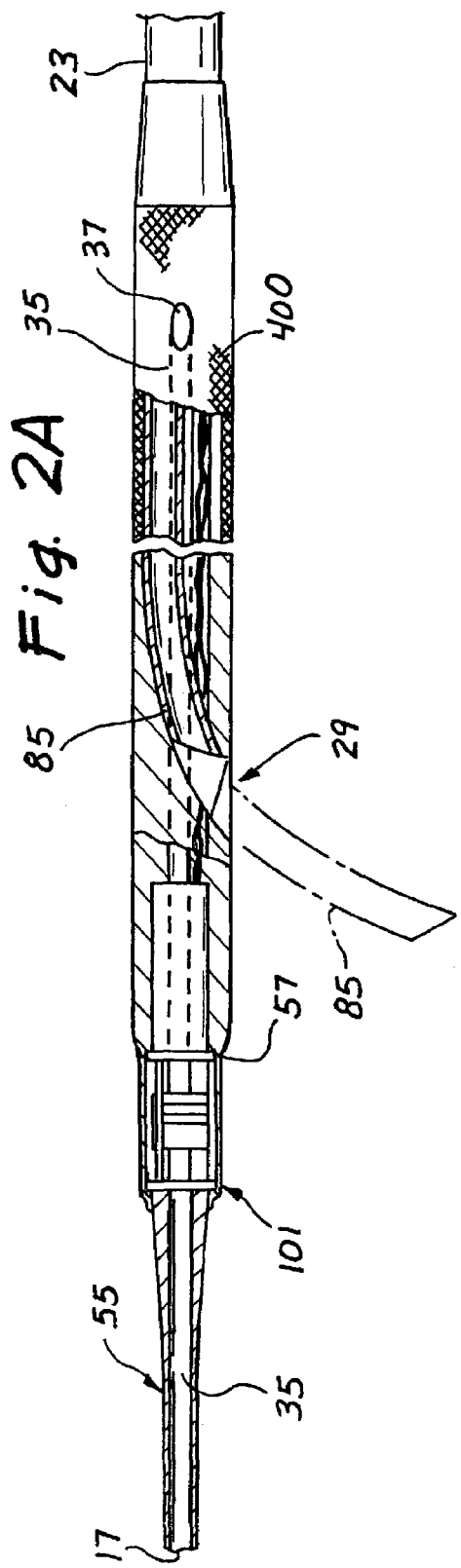

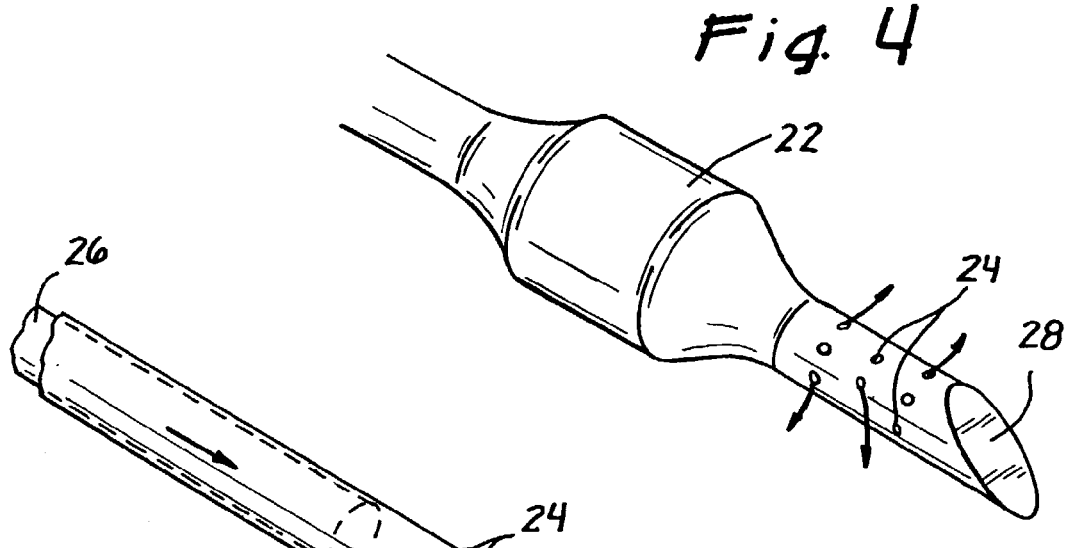
Fig. 4
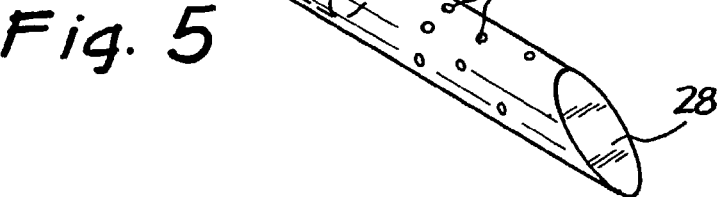
Fig. 5
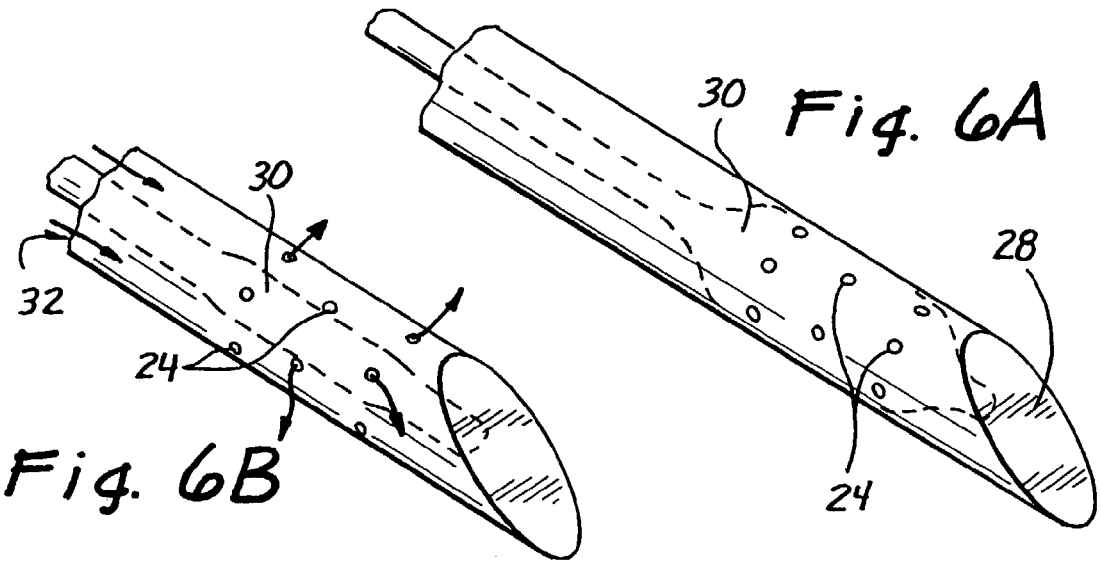
Fig. 6A
Fig. 6B
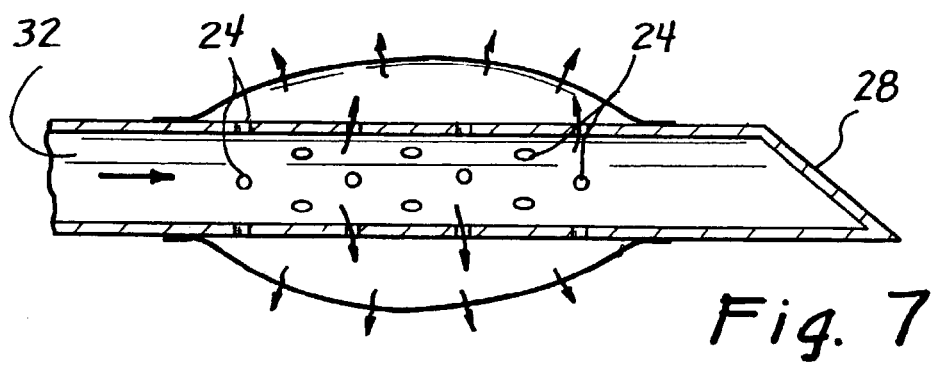
Fig. 7

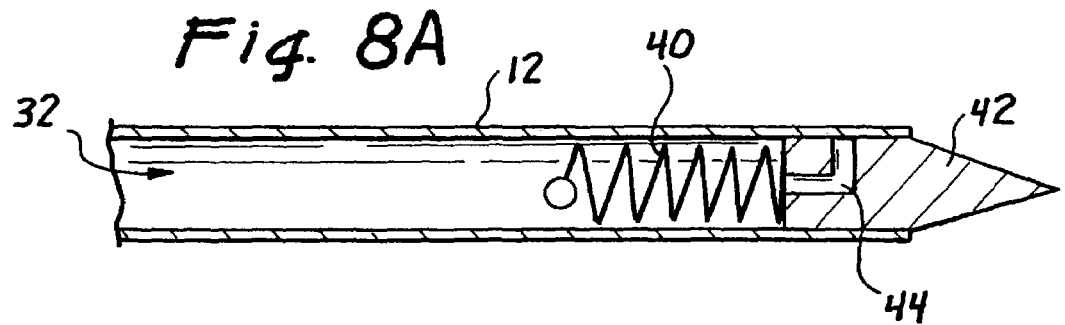
Fig. 8A
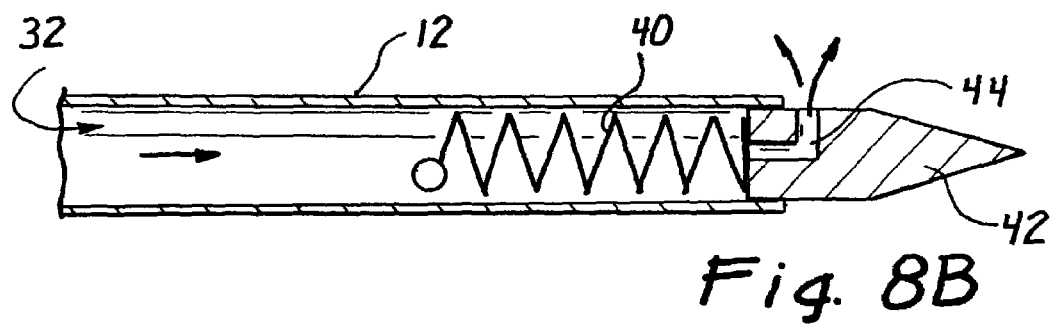
Fig. 8B
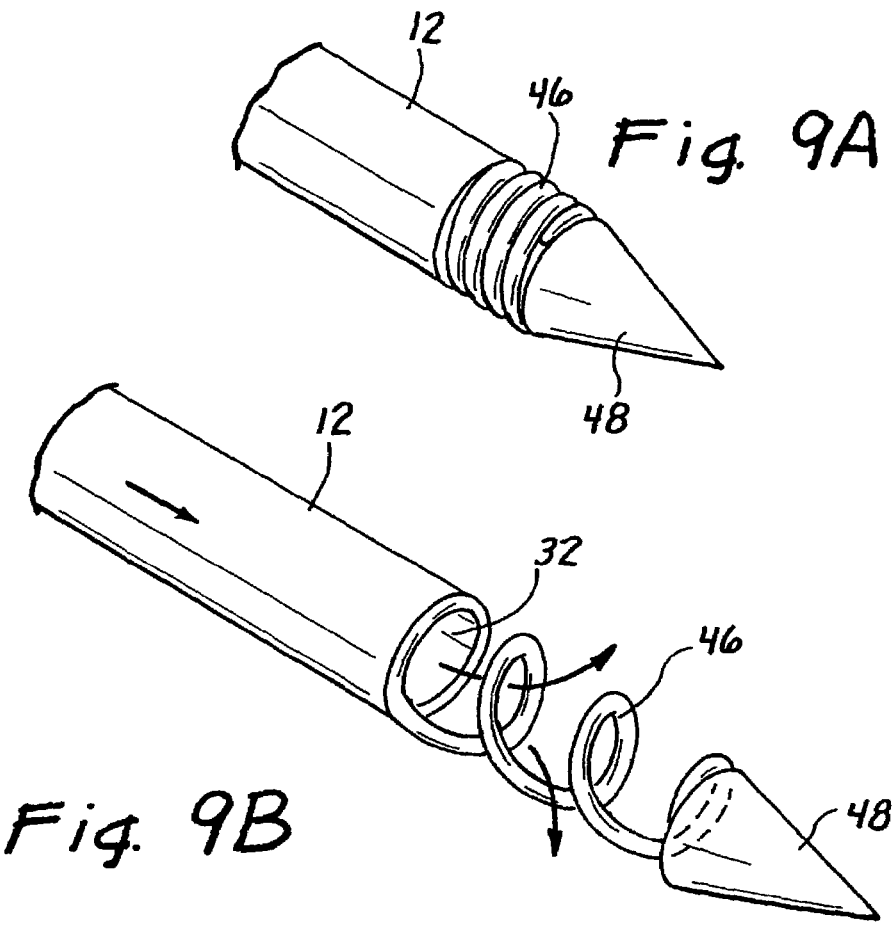
Fig. 9A
Fig. 9B

METHODS AND APPARATUS FOR ACUTE OR CHRONIC DELIVERY OF SUBSTANCES OR APPARATUS TO EXTRAVASCULAR TREATMENT SITES This is a continuation of application Ser. No. 09/766,502 filed on Jan. 17, 2001 now U.S. Pat. No. 6,602,241.

BACKGROUND OF THE INVENTION

There exist many situations in which it is desirable to deliver substances (e.g., drugs, biological materials, etc) or apparatus (e.g., wires, sensors, etc.) to specific locations within tissues (i.e. an "interstitial target site") of the body of a human or veterinary patient. Examples of the types of tissues wherein such target sites may be located include myocardial tissue, brain tissue or tumors.

Some catheters and drug delivery stents of the prior art have been purportedly useable to indirectly deliver drugs or substances to specific interstitial target locations by first dispensing the drug within the lumen of a nearby blood vessel or on the inner surface of a nearby blood vessel and then allowing the drug to migrate through the blood vessel wall or through a downstream capillary bed, to the desired interstitial target location.

The prior art has also included catheter devices that may be used for delivering substances or apparatus directly into interstitial target locations by guided advancement of a penetrating cannula or needle from a catheter located within the lumen of a nearby blood vessel, through the wall of the blood vessel and through any intervening tissue, to the interstitial target site. The desired substance or apparatus may then be infused or delivered directly into the target interstitial site without any need for transmural diffusion through the blood vessel wall or downstream transluminal flow to the selected capillary bed. Examples of these catheter devices useable for direct delivery of drugs or apparatus into interstitial target sites are described in PCT International Patent Publications No. PCT/US99/07115 and PCT/US99/07112.

Particular interest has developed in methods for controlled or targeted delivery of substances such as drugs (e.g., chemotherapeutic agents), gene therapy compositions (e.g., plasmids, viral vectors, genetically modified cells, naked DNA), biological factors (e.g., angiogenic factors, nerve growth factors, other cell growth factors, other proteins), monoclonal antibodies, or specific cell types (e.g., stem cells or other progenator cells, pancreatic islet cells, dopamine secreting neurons, endothelial cells, myocardial cells, other myocytes, etc) into interstitial target locations for the purpose of treating diseases such as myocardial ischemia, solid tumor types of cancer, parkansonism, diabetes, etc. Specifically, in the treatment of myocardial ischemia, research has indicated that introduction of certain angiogenic substances into ischemic areas of myocardium may result in "therapeutic angiogenesis" in patients who suffer from clinically significant coronary artery disease. Generally speaking, the term "angiogenesis" refers to the creation of new capillaries and/or blood vessels within the parenchyma of an organ, within a tumor or within an area of tissue (e.g., myocardium). Angiogenesis is believed to occur as a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane. The term "therapeutic angiogenesis" involves the administration of angiogenic substances or treatments to promote one or more steps in the angiogenesis process thereby providing for the creation of new blood flow in tissue that previously lacked sufficient blood flow.

Various approaches have heretofore been used for delivery of angiogenic substances into the myocardium. One approach is the use a tissue penetrating device such as a laser to create penetration tracts or transmyocardial (TMR) channels which extend from either the epicardial (outer) surface or endocardial (inner) surface of the heart into the myocardium, and to then inject quantities of angiogenic substances into those TMR channels. Examples of this approach are described in U.S. Pat. No. 5,925,012 (Murphy-Chutorian, et al.), U.S. Pat. No. 5,999,678 (Murphy-Chutorian, et al.) And U.S. Pat. No. 6,106,520 (Laufer, et al.)

There remains a need in the art for the development of new apparatus and methods for delivering substances or apparatus to specific target sites within tissues, tumors or organs of the body with minimal trauma to the tissues and optimum control as to the precise location(s) at which the substances or apparatus are introduced.

SUMMARY OF THE INVENTION

In accordance with the invention, there is provided a system comprising a) a vessel wall penetrating catheter that is positionable within a blood vessel of a human or animal patient and which has a vessel wall penetrator advanceable from the catheter, outwardly through the wall of the blood vessel in which the catheter is positioned, in the direction of an extravascular target site and b) a delivery catheter that is advanceable from the penetrator to the target site. Substance(s) or apparatus may then be delivered to the target site through the delivery catheter and/or samples of body fluid or other information may be obtained from the target site through the delivery catheter. In applications where it is desired to use the delivery catheter continuously or intermittently over an extended period of time (e.g., hours, days, weeks or months) the penetrator may be withdrawn into the vessel wall penetrating catheter and the vessel wall penetrating catheter may be removed, leaving just the delivery catheter in place (e.g., extending through the patients blood vessel(s), outwardly through the penetration formed in the blood vessel wall and to the target site.) The types of substances that may be delivered through the delivery catheter include drugs (thrombolytics, platelet inhibitors, anti-restenotic agents, beta blockers, ion channel antagonists, positive or negative ionotropic agents, anti-arrhythmics, antibiotics, analgesics, chemotherapeutic agents, other anti-neoplastic agents, etc.), natural or recombinant proteins (e.g., angiogenic proteins such as vascular endothelial growth factor (VEGF), fibroblast growth factors (FGF), epidermal growth factor (EGF), platelet-derived growth factor (PDGF) nerve cell growth factor (NGF) or hepatocyte growth factor (HGF)), cells or cellular preparations (e.g., stem cells, other progenetor cells, myocytes, myoblasts, pancreatic islet cells, dopamine secreting cells, etc), genes or gene therapy preparations (e.g., viral vectors containing genes for gene therapy applications, genetic material for electrophoretic transmission into cells, plasmids, viral vectors, genetically modified cells, naked DNA, etc.), contrast media or dyes for imaging, radiolabeled diagnostic materials or drugs or other traceable substances, mixtures of any of the above, alone, in solution or in combination with any delivery substance or matrix (e.g., polymer matrices used to inhibit or slow distribution or dissemination of a substance away from its original injection site), dialysis solutions or micro-dialysis solutions, or any other type of substances that may be introduced through the delivery catheter for any therapeutic, imaging, diagnostic or other purpose.

Further in accordance with the invention, the types of target tissues into which the delivery catheter of the above-described system may be placed include various organs (e.g., heart, brain, liver, pancreas), the walls of blood vessels (by injection directly into the vessel wall or by injection into a periadventital area outside of but close to the vessel so that the drug or substance will be distributed into the vessel wall), muscles (e.g., myocardium, skeletal muscle) or aberrant masses (e.g., tumors, cysts).

Still further in accordance with the invention, substances delivered through the delivery catheter may be of increased viscosity to deter their egress from the target area, may be adherent to tissues in the target area so as to deter egress of the substance from the target area and/or may harden or form a mass in situ after injection into the target area, thereby deterring egress of the substance from the target area.

Still further in accordance with the invention, the outlet port(s) of the delivery catheter may be configured such that substances injected through the delivery catheter will form high pressure jet sprays into the tissue surrounding the delivery catheter.

Still further in accordance with the invention, the vessel wall penetrator of the vessel wall penetrating catheter and/or the delivery catheter may be equipped with backflow deterrent for limiting or preventing fluid that is injected through the delivery catheter from bleeding back through the tissue tract through which the delivery catheter and/or penetrator was/were advanced. In chronic dosing applications wherein the delivery catheter remains indwelling, such backflow deterrent may comprise a balloon, annular rib or other barrier formed on the outer surface of the delivery catheter to block the backflow of fluid through the tract in which the delivery catheter resides. In acute dosing applications wherein the delivery catheter is extracted and removed immediately after injection of the substance, the backflow deterrent may comprise a) an embolizing member such as a detachable blocker, balloon, clot, fibrin, bead of polyvinyl alcohol, etc. that is deployed into the tissue tract as the delivery catheter and/or penetrator is/are retracted, b) a substance such as a cyanoacrylate, polyethylene glycol, hydrogel, fibrin glue or other material is injected to embolize, seal or close the tract through which the delivery catheter and/or penetrator was/were advanced or c) a tissue fusing device, such as a radio-frequency emitting electrode, for welding or fusing adjacent tissue in a way that effectively closes the tract through which the delivery catheter and/or penetrator was/were advanced.

Still further in accordance with the invention, the delivery catheter of the above-described system may be used for aspiration of samples of blood or body fluid from the target site and/or may include one or more interactive members, such as emitters, detectors, electrodes, sensors, etc. for a) facilitating the delivery catheter's penetration through tissue, b) facilitating the distribution of an injected substance into surrounding tissues (e.g., by iontophoresis), c) creating a pocket into which a substance may be injected or d) sensing the position of the delivery catheter or some content or variable (e.g., ECG, contractility, force of contraction, pressure, local ECG amplitude, local protein levels, local antibody levels, $pO_2$, $pCO_2$, oxygen saturation, blood flow rate, pH, local lactate levels, etc.) of the adjacent tissue.

Still further in accordance with the invention, the delivery catheter may be used to continuously or intermittently monitor physiological parameters or variables (e.g., rate of blood flow away from the site) or pharmacokinetic or biodistributive parameters or variables (e.g., the rate at which a substance will distribute away from the target site, how long the injected substance may be expected to remain at the target site, the rate at which the injected substance may be inactivated or metabolized at the target site and/or other parameters/variables relating to the activity of the substance after it has been injected at the site). Such information may then be used to verify that the delivery catheter is suitably placed for optimal or desired therapeutic effect of an injected substance or apparatus delivered to the site. If it is determined that an injected substance is likely to distribute away from the target site too quickly, or remain at the target site for too long, or become inactivated too quickly or not quickly enough, the delivery catheter may be reposition to a site that is more desirable. Similarly, if it is determined that the site is too vascularized or not vascularized enough for the desired therapeutic or diagnostic activity of the delivered substance or apparatus, the delivery catheter may be repositioned to a new target site that is suitably vascularized, before continuing with delivery of the substance or apparatus through the delivery catheter. One example of a manner in which this type of site monitoring may be accomplished is to deliver radio-opaque dye, a radio-labeled substance or other traceable material through the delivery catheter and to the location adjacent the outlet port(s) of the delivery catheter (i.e., the target site to which the therapeutic or diagnostic substance is being or will be delivered) Thereafter, the rate at which that traceable substance distributes away from that site (or the rate at which it becomes inactivated, degraded or metabolized) may be measured by appropriate means such as x-ray (when radio-opaque traceable material is used) or radio-scanning (when radio-labeled traceable material is used). If the site is deemed to be acceptable, the therapeutic or diagnostic substance or apparatus may be delivered to the site. If the site is deemed to be unacceptable (or less than optimal) the delivery catheter may be repositioned and the test may be repeated. In some applications, the delivery catheter may have multiple lumens such that a therapeutic or diagnostic substance or apparatus may be delivered through one lumen and a traceable substance useable for site monitoring/verification may be delivered through another lumen.

Still further in accordance with the invention, the delivery catheter of the above-described system may include anti-obstruction apparatus (e.g., a mandrel, stylet, inflatable member or semi-permeable barrier) that allows the desired substances or apparatus to be introduced in the distal direction through the delivery catheter but prevents cellular ingrowth or other matter from invading and obstructing the lumen and/or outlet port(s) of the delivery catheter. In this manner, the delivery catheter remains patent, even when it has been indwelling within tissue for an extended period of weeks or months.

Still further in accordance with the invention, the efficacy of substances injected through the delivery catheter may in some applications be enhanced by limiting the rate at which the substance distributes away from the site or otherwise altering the biodistribution and/or pharmacokinetics of the substance after it has been introduced into the body. This may be accomplished by introducing the substance in the form of a solid, dry pellet, implant, filament or gel. Alternatively, this may be accomplished by micro-encapsulating or mixing the substance with a polymer matrix, oil or other drug delivery matrix or material that is prepared before injection or formed in situ or by forming liposomes or colloidal suspensions containing the substance, etc. Another way in which this may be achieved is by causing the substance to promptly enter cells rather than allowing the substance to remain disposed in intercellular fluids or intercellular spaces from which the substance my quickly distribute or disseminate away from the injection site (e.g., by driving the substance into adjacent cells by electrophoretic means or chemical means, by modifying the properties (e.g., solubility, polarity, pH) of the substance in a manner which will facilitate its transport into cells, by atomizing or spraying the substance as it exits the catheter, or by causing the substance to exit the catheter at increased velocity or force.

The invention together with additional features and advantages thereof may best be understood by reference to the following description taken in connection with the accompanying illustrated drawings.

BRIEF DESCRIPTION OF THE DRAWINGS

FIG. 1 is a schematic showing of a human patient who is undergoing a procedure for transvenous placement of a delivery cannula for ongoing delivery of drugs or apparatus to an ischemic region of the patient's myocardium.

FIG. 2 is a broken, side view of one embodiment of a catheter system of the present invention.

FIG. 2*a* is an enlarged, cut-away view of section 2*a* of FIG. 2.

FIGS. 2*b*-2*d* show, in step-by-step fashion, the manner in which the catheter system of FIG. 2 may be used to accomplish transluminal placement of a delivery catheter for delivery of substances or apparatus to an extravascular target location.

FIG. 3*a* shows an embodiment of a delivery catheter of the present invention which incorporates a subcutaneous injection port for periodic infusion of fluids through the delivery catheter.

FIG. 3*b* shows an embodiment of a delivery catheter of the present invention which incorporates an exteriorized Luer fitting for attachemt of a syringe to the delivery catheter for periodic infusion of fluids through the delivery catheter.

FIG. 4 is a partial perspective view of a delivery catheter of the present invention having a plurality of side apertures for disseminated outflow of fluid therefrom and a balloon for preventing injected fluid from backflowing through the tract through which the delivery catheter extends.

FIG. 5 is a partial perspective view of a delivery catheter of the present invention having a plurality of side apertures for disseminated outflow of fluid therefrom and a stylet member that is insertable into the lumen of the delivery catheter to block the side apertures at times when no fluid is being infused through the delivery catheter.

FIG. 6*a* is a partial perspective view of a delivery catheter of the present invention having a plurality of side apertures for disseminated outflow of fluid therefrom and any inflatable obturator position within the lumen of the delivery catheter in an inflated state wherein the obturator blocks the side apertures at times when no fluid is being infused through the delivery catheter.

FIG. 6*b* is a partial perspective view of the delivery catheter of FIG. 6 wherein the obturator is in a deflated state such that fluid may be infused through the lumen of the delivery catheter and out of the side apertures.

FIG. 7 is a partial longitudinal sectional view of a delivery catheter the present invention having a plurality of side aperture is for disseminated outflow of fluid therefrom and a semi-permeable diffusion barrier mounted about the catheter such that fluid infused through the lumen of the delivery catheter and out of the side apertures will collect within the diffusion barrier and will subsequently diffuse outwardly through the barrier while the diffusion barrier prevents cellular matter or other material from invading and obstructing the side apertures or lumen of the delivery catheter.

FIG. 8*a* is a partial longitudinal sectional view of a delivery catheter the present invention having an open distal end and a spring mounted tip member having a fluid outlet channel formed therein, such tip member being in a retracted position wherein the fluid outlet channel is fully covered by the catheter body and cellular matter or other material is prevented from invading and obstructing the fluid outlet channel.

FIG. 8*b* is a partial longitudinal sectional view of the delivery catheter of FIG. 8*a*, wherein fluid is being infused in the distal direction through the lumen of the delivery catheter and the pressure of the fluid has advanced the distal tip member to an extended position wherein the fluid outlet channel uncovered and fluid is permitted to flow from the lumen of the delivery catheter, outwardly through the fluid outlet channel.

FIG. 9*a* is a partial perspective view of a delivery catheter the present invention having an open distal end and a coil spring mounted tip member mounted thereon, such tip member being in a retracted position wherein the convolutions of the coil spring are contracted into abutting contact with each other, thereby closing the lumen of the delivery catheter and preventing cellular matter or other material from invading and obstructing the lumen of the delivery catheter.

FIG. 9*b* is a partial perspective view of the delivery catheter of FIG. 9*a* wherein fluid is being infused in the distal direction through the lumen of the delivery catheter and the pressure of the fluid has advanced the distal tip member to an extended position wherein the convolutions of the coil spring are spaced apart and fluid is permitted to flow from the lumen of the delivery catheter, outwardly through the spaces between the convolutions of the coil spring.

FIG. 10 is a diagram of a human heart showing the manner in which a delivery catheter of the present invention may be transvenously implanted within an interstitial target site of the myocardium.

FIG. 10*a* is an enlarged, cut-away view of a portion of FIG. 10, showing the manner in which the delivery catheter extends through the wall of a coronary vein and in generally tangential relationship to the adjacent left ventricle of the heart.

FIG. 11 is a diagram of a human heart showing the manner in which a delivery catheter of the present invention having a backflow preventing balloon thereon may be positioned within a coronary vein to deliver a substance to a target region of the myocardium by selective, retrograde infusion through the coronary vein.

FIG. 12 is an enlarged, cut-away view of a portion of FIG. 11, showing the backflow preventing balloon in an inflated state and a substance being infused through the delivery catheter and through the coronary vein in the retrograde direction.

FIG. 13 is a partial, side view of a vessel wall penetrating catheter of the present invention showing the varying angles at which the vessel wall penetrating member may be deployed, relative to the longitudinal axis of the catheter body, depending on the extent to which the vessel wall penetrating member has been advanced.

DETAILED DESCRIPTION OF PREFERRED EMBODIMENTS

The following detailed description, and the drawings to which it refers, are provided for the purpose of describing and illustrating certain examples or embodiments of the invention only and are not intended to exhaustively describe or show all possible embodiments or examples of the invention.

Generally, one method of the present invention may carried out by first inserting a vessel wall penetrating catheter into the vasculature of a human or veterinary patient, advancing the vessel wall penetrating catheter through the vasculature to a location within a blood vessel that is adjacent or near a target location at which a substance (e.g. a drug, biological or therapeutic agent) or apparatus (e.g. a sensor) is to be delivered and thereafter advancing a vessel wall penetrator from the catheter, transmurally through the wall of the blood vessel, in the direction of the target location. In some embodiments, the vessel wall penetrator itself may comprise a tubular member through which a substance or apparatus may be passed. In those embodiments, the penetrator will be advanced all the way to the target location(s) and the substance or apparatus will then be infused or delivered through the lumen of the penetrator. In other embodiments, a separate delivery catheter will be advanced through the vessel wall penetrator to the target location and, thereafter, the vessel wall penetrator may be withdrawn and removed (along with the entire vessel wall penetrating catheter) leaving only the delivery catheter in place. This secondary catheter may then remain indwelling for whatever period of time is desired, to allow samples to be withdrawn from the target location or to allow therapeutic agents and/or apparatus (e.g. wires or sensors) to be introduced to the target location at desired intervals or on a desired schedule.

Figure 2B:
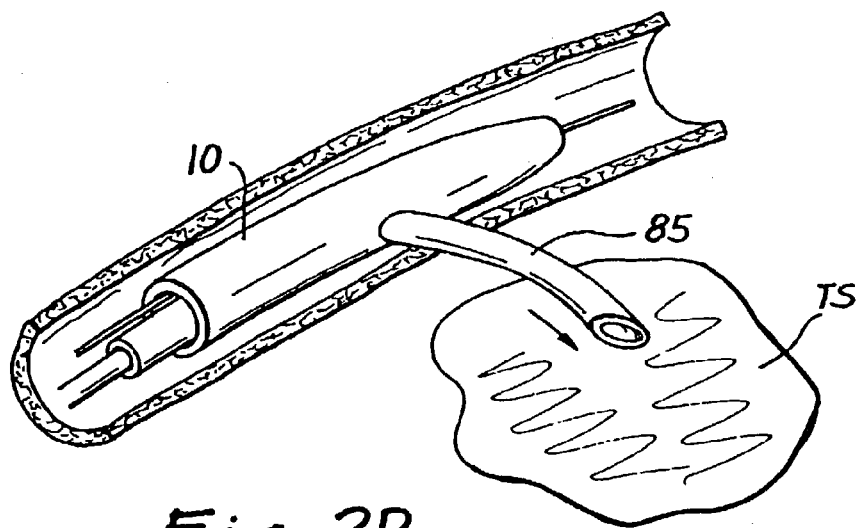
Figure 2C:
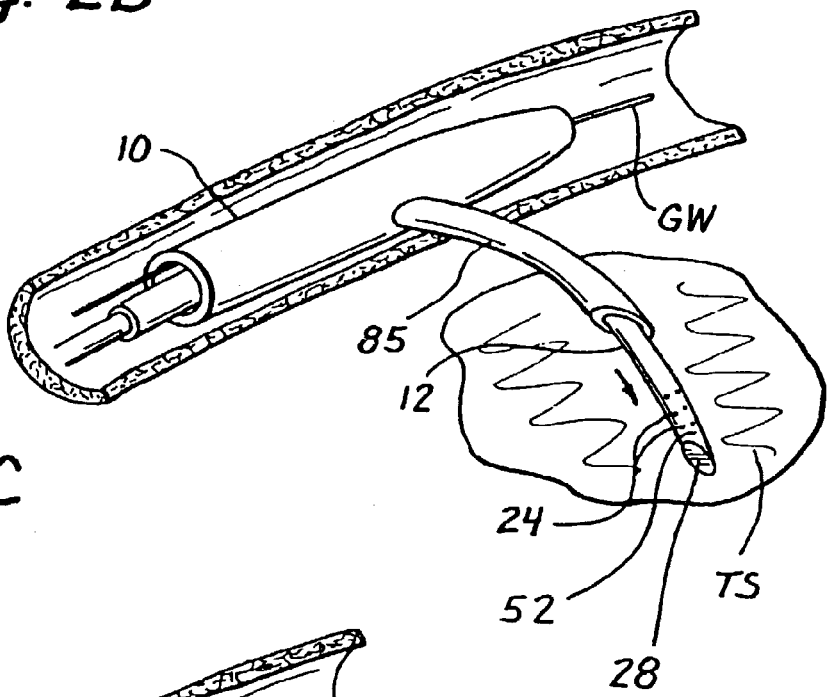
Figure 2D:
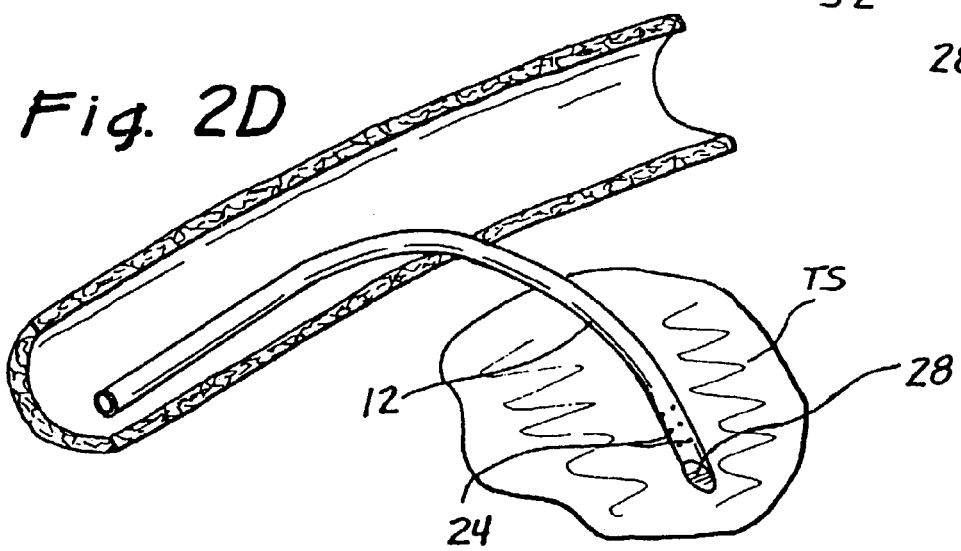

A. Transluminally Deployable Catheter System for Acute or Chronic Delivery of Substances or Apparatus to Interstitial Target Sites:

FIGS. 2-2d show an example of a catheter system 10 of the present invention. This system 10 comprises the combination of a vessel wall penetrating catheter 11 and a delivery catheter 12. FIG. 1 shows this catheter system 10 in use on a human patient.

Vessel Wall Penetrating Catheter

In the embodiment illustrated, the vessel wall penetrating catheter 11 includes an elongated catheter body 13 having a proximal end 15, a distal end 17, a handle 19 and a hub 21 coupled to the proximal end of the catheter body and to the handle. The handle 19 may also serve as a controller for use in advancing and retracting the vessel wall penetrator 85, as described more fully below.

Figure 3A:
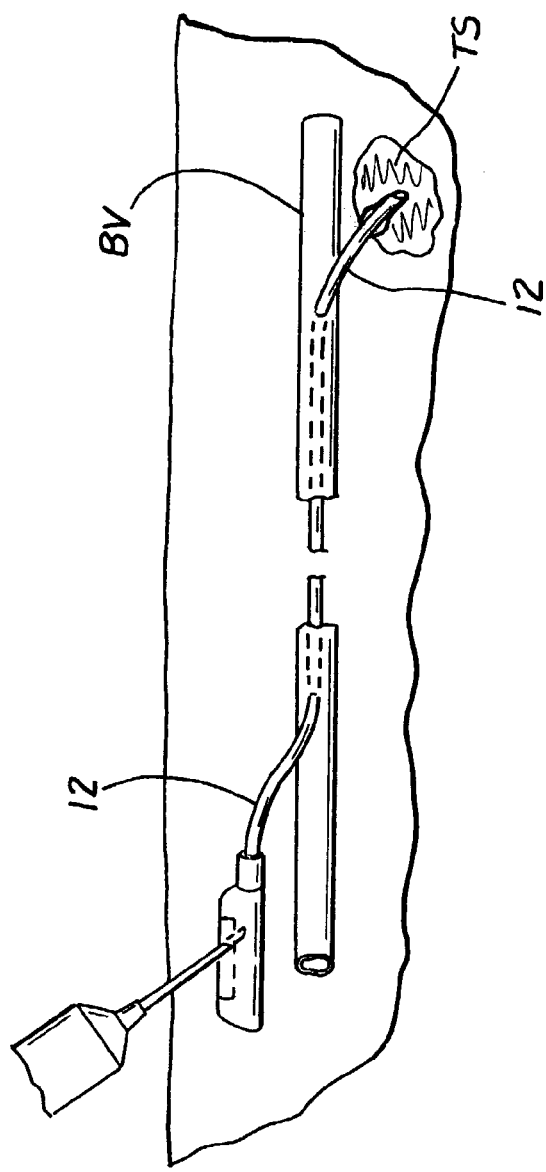

The vessel wall penetrating catheter body 13 includes a relatively rigid proximal section 23 shown in FIGS. 2 and 3a which may be constructed, for example, of a metal hypo tube and an elongated flexible distal section or region 25 suitably joined to the proximal section. At least the distal section 25 is sized to be received within a coronary artery, and therefore can be received within either a coronary artery or a coronary vein. The catheter body section 13 has a penetrator lumen 27 which terminates distally at an exit location or exit port 29 that is located on a peripheral wall 31 of the catheter body. A vessel wall penetrator, such as a hollow NiTi needle as shown in FIGS. 2a (phantom lines), 2b and 2c, is disposed within the penetrator lumen 27 and is advanceable out of the side exit port 29 as seen in FIGS. 2a-2c. The exit port 29 is preferably located a short distance proximally of the distal end 17. A radiopaque marker 33 may be mounted on the lumen 27 adjacent the exit port 29 to facilitate placement and positioning of the vessel wall penetrating catheter 11.

The catheter body 13 also has a guidewire lumen 35 (FIG. 3a) which extends to the distal end 17 of the catheter body 15. In this embodiment, the guidewire lumen 35 extends proximally to an inlet port 37 at the peripheral wall 31 closely adjacent the proximal section 23.

Figure 3B:
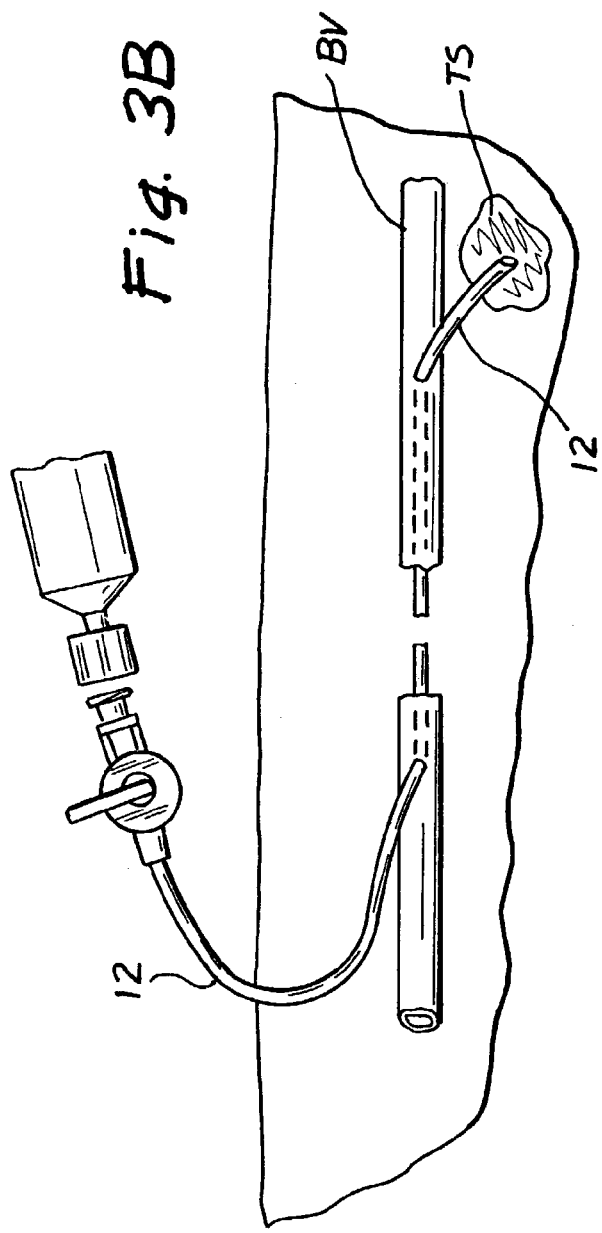
Figure 10:
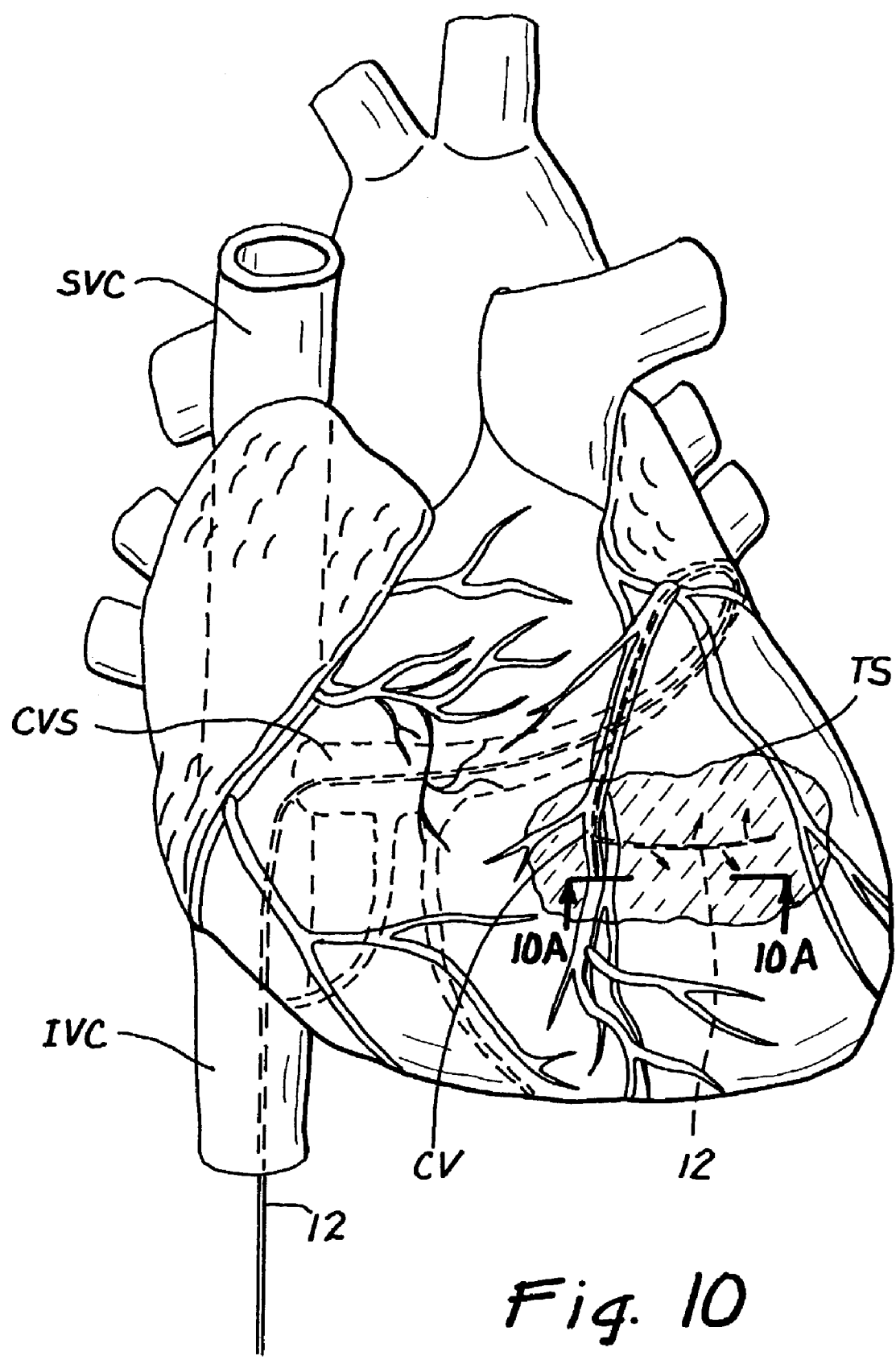

A major section 51 of the catheter body 13 terminates distally in a distal opening 53, and the catheter body includes a distal tip section 55 of soft, flexible, biocompatible material (FIGS. 3a and 3b). A proximal portion 56 of the distal tip section 55 is received in the distal opening 53 and a distal portion of the distal tip section extends distally to the distal end 17. The distal portion of the distal tip section 55, i.e. the portion of the distal tip section 55 which extends beyond the distal end of the major section 51 is of smaller cross sectional area than the adjacent region of the major section to thereby define an annular shoulder 57 on the catheter body 13. The exit port 29 is spaced slightly proximally of the shoulder 57.

Guidance Elements

In many embodiments, it will be desirable for the vessel wall penetrating catheter 11 to include a guidance element for guiding the positioning and rotational orientation of the catheter 11 within the vasculature such that the vessel wall penetrator 85 will be properly aimed in the direction of the target site. Such guidance element may include marker(s), imaging apparatus, emitter(s), sensor(s) etc. In the particular embodiment shown in FIGS. 2a and 2b, the guidance element comprises the combination of an imaging transducer 81 and an imageable marker assembly 101. The imaging transducer 81 is fixedly mounted on the catheter 11, and in the embodiment illustrated in FIG. 3a, the imaging transducer is mounted on the distal tip section 55 just distally of the shoulder 57. In this embodiment, the imaging transducer 81 is a phased array transducer and is operative to image 360° about the vessel wall catheter 11. The imaging transducer 81 is coupled to a multiplex circuit 83 which is within the major section 51 of the catheter body 13 adjacent the shoulder 57, and the multiplex circuit 83 is in turn coupled to leads 85 which extend through the lead lumen 39, through the handpeice 19 and are attached to a connector 86 which allows the leads 39 to be connected to a viewing instrument and screen. When activated, the imaging transducer emits ultrasound signals and receives back echos or reflections which are representative of the nature of the surrounding environment. The imaging transducer provides an imaging signal from which an image of the surrounding structure can be created on a screen of the viewing instrument. In a preferred practice of this invention, the phased array transducer, the accompanying circuitry and the separate viewing instrument/screen may be obtained from Endosonics, Inc. of Rancho Cordova, Calif.

In an alternate embodiment of this invention, the imaging element may be formed of a single rotating crystal or transducer. In this embodiment the transducer would have a single lead out, would include a drive shaft which would run back to the proximal end of the catheter through 39.

In the particular embodiment shown, an imageable marker 101 is fixedly mounted on the catheter body 13 in a known circumferential orientation relative to the exit port 29. This marker 101 may be in the form of a structure or cage, as shown, and the transducer 81 may be located within the marker cage or marker structure. In the embodiment shown, the marker cage comprises a plurality of longitudinal members 103 disposed at circumferentially spaced apart locations about a hollow interior space 105. The hollow space 105 receives the distal tip section 55 and the transducer 81, and the transducer 81 is an onboard transducer in that it is inseparable from and not removable from the catheter body 13. One of the longitudinal members is located at a circumferential position that is axially aligned with the exit port 29 and consequently is also axially aligned with the path that will be followed by a tissue penetrator that is advanced from the catheter body 13 through the exit port. Thus, the imageable marker 101 forms on the image obtainable from the imaging signal from the imaging transducer a penetrator path indication that indicates the path that will be followed by the tissue penetrator when the tissue penetrator is advanced from the catheter. As an alternative to the use of a marker 101, the path that will be followed by the penetrator may be indicated on the image by electronic means or by the use of a computer program, thereby eliminating the need for a penetrator path indicating marker 101. In many embodiments, the marker 101, electronic penetrator path indicator or computer program for determination of the penetrator path may not only indicate the trajectory or path of the penetrator but may also indicate a stopping point at which advancement of the penetrator will stop or is intended to stop. By providing such an indication of the mandatory or intended stopping point of the penetrator advancement, the operator may case the penetrator to be optimally positioned at the intended site without advancing the penetrator too far as may result in missing of the intended delivery site or unwanted penetration of a blood vessel or other anatomical structure that lies beyond the site at which the penetrator is desired to stop.

With the construction described above, the imaging transducer 81 and the marker 101 are both mounted on the distal tip section 55 which has a smaller cross sectional area than does the adjacent region of the major section 51 of the catheter body 13. Accordingly, the cross sectional area of the catheter body 13 at the region containing the imaging transducer 81 and the marker 101 can still be relatively small. Also, the exit location 29 is closely adjacent to the imaging transducer 81 and may be, for example, about 5 mm from the imaging transducer. This minimizes the likelihood of any significant torsional displacement of the exit location 29 relative to the marker 101 and imaging transducer 89. It may also be appreciated that the imaging transducer may be mounted such that the exit port is located directly at the point at which the transducer is affixed to the catheter, illuminating any displacement.

It will be appreciated that various other types of imaging or position sensing apparatus may be used as alternatives to the above-described imaging transducer 89/marker 101 combination to guide and orient the vessel wall penetrating catheter 11. For example, the vessel wall penetrating catheter 11 may incorporate an emitter that is useable in conjunction with an electromagnetic, potentiometric, or other electro-anatomical mapping and/or catheter guidance/positioning systems, such as those commercially available from or under development by Biosense Webster, Inc., Diamond Bar, Calif.; Cardiac Pathways Corporation, 995 Benicia Avenue, Sunnyvale, Calif. and/or Stereotaxis, Inc., 4041 Forrest Park Avenue, St. Louis, Mo. Examples of these types of catheter guidance or positioning systems are described in U.S. Pat. No. 5,820,568 (Willis), U.S. Pat. No. 5,931,818 (Werp et al.), U.S. Pat. No. 5,654,864 (Ritter et al.), U.S. Pat. No. 5,928,248 (Acker), U.S. Pat. No. 5,752,513 (Acker et al.), U.S. Pat. No. 5,558,091 (Acker et al.) And U.S. Pat. No. 5,833,608 (Acker), the entire disclosures of which are expressly incorporated herein by reference.

Delivery Catheter

After the vessel wall penetrator 85 has been advanced to the desired extended position, the delivery catheter 12 may be advanced through the lumen of the penetrator 85 and out of its distal end. For applications where it is desired for the delivery catheter 12 to penetrate into myocardial tissue, the delivery catheter 12 may comprise a small cannula, hypotube or microcatheter formed of a suitable material such as polyimid, polytetrafluoroethylene, polypropylene, polyethylene, Pebax™, etc. For many applications, including application wherein the delivery catheter 12 is used to deliver substances into the myocardium, the delivery catheter 12 may have an outer diameter of approximately 0.25-0.5 mm. In embodiments where it is intended for the delivery catheter to penetrate through tissue as it advances the distal tip of the delivery catheter 12 may be beveled or sharpened. Optionally, the delivery catheter 12 may have an energy emitting distal tip for enhanced tissue penetrating capability. For example, a radiofrequency electrode may be located on or near the distal tip of the delivery catheter to provide for tissue penetration enhanced by RF energy emission. Or, the delivery catheter may be adapted to ultrasonically vibrate, thereby improving its ability to penetrate through tissue.

The body of the delivery catheter 12 may be radio-opaque or one or more radio-opaque markers may be formed on the delivery catheter (e.g., at its distal tip) to permit imaging of the catheter and determination of the position of the catheter within the patient's body.

In some applications, such as those where drugs, substances or apparatus are to be chronically delivered to the target site over a period of days, weeks or months, the delivery catheter will be allowed to remain indwelling after the vessel wall penetrating catheter 11 has been removed. To facilitate this, a detachable or removable Luer connector 47 may mountable proximal end of the delivery catheter 12 as shown in FIGS. 2 and 3b. This detachable or removable Luer connector may be removed when during proximal withdrawal and removal of the vessel penetrating catheter 11 while the delivery catheter 12 remains in place. Thereafter, in embodiments wherein the proximal end of the delivery catheter 12 remains exteriorized, the removable or detachable Luer connector 47 may be attached to the exteriorized proximal end of the delivery catheter 12 and may thereafter be used for subsequent attachment of a stopcock 47 and/or syringe 50 as shown in FIG. 3b. In other embodiments, the proximal end of the delivery catheter 12 may be devoid of any hub or connector and may be connected to a pump, delivery device, subcutaneously implanted reservoir or injection port 52, as shown in FIG. 3a.

An opening for infusion or aspiration of substances/apparatus may be formed in the distal end of the delivery catheter 12 and/or one or more fluid outlet openings may be formed in the sidewall of the delivery catheter 12, near its distal end, as shown in FIG. 2c or 2d. For many applications, one or more openings may be laser drilled into the delivery catheter 12, such openings being no more than ½ the diameter of the catheter lumen through which the substance is being injected, such that high pressure jets of the substance will be created as the substance exits the delivery catheter 12. The creation of such elevated pressure as the substance exits the delivery catheter 12 serves to propel or drive the substance through cell membranes and into intracellular spaces cells rather than allowing the substance to remain in intercellular spaces (i.e., spaces or fluids between cells or outside of the cells) from which the substance would more rapidly distribute away from the injection site.

Interactive Apparatus on Delivery Catheter

As shown in FIG. 2c, one or more interactive members 52 such as sensors, emitters, etc. . . . may be positioned on or near the distal end of the delivery catheter 12 for emitting energy as described above or for sensing, sampling or receiving information from the tissues adjacent the distal portion of the delivery catheter 12. Interactive members that comprise sensor(s) may provide information on the position of the delivery catheter 12 or measurements of variables such as ECG, contractility, force of contraction, pressure, local ECG amplitude, local protein levels, local antibody levels, $pO_2$, $pCO_2$, oxygen saturation, blood flow rate, pH, local lactate levels, etc. By use of such information received from the target site, the clinician may assess or characterize the target site to ascertain its suitability before introducing a substance or apparatus into the target site.

In applications where it is desired to facilitate the passage or distribution of an injected substance into the surrounding tissue, the interactive member 52 may emit some facilitating energy, such as an electromagnetic field for iontophoretic transmission of the substance through the adjacent tissue.

In other applications, the interactive member 52 may emit energy, such as radiofrequency energy, that will create a pocket in the surrounding tissue such that a substance or apparatus my be introduced into that pocket. The walls of the pocket may be seared by the energy so as to slow the distribution of the substance out of the pocket.

In other applications, the interactive member 52 may emit energy, such as ultrasound, that facilitates distribution of a substance by permeating cell membranes or by vibrating the catheter tip.

Apertures for High Pressure Injection from Delivery Catheter

As shown in FIGS. 2c and 2d, the distal end of the delivery catheter may be closed and a plurality of small side apertures 24 may be formed in the sidewall of the delivery catheter 12 to provide for high pressure outflow of fluid from the deivery catheter and into the surrounding tissues.

Backflow Deterrent Apparatus on Delivery Catheter and/or Penetrator

In some applications, the injection of fluids through the delivery catheter 12 into a closely confined space or interstitial site may result in some regurgitation or backflow of the injected fluid through the tract through which the vessel wall penetrator 85 and/or delivery catheter 12 were advanced. In acute dosing situations where the delivery catheter is removed immediately after the dose, this backflow of the injected fluid may be prevented by sealing the penetration tract or by introducing a material (e.g., an adhesive or embolizing material) into the tract during immediately after removal of the catheter 12. This may be accomplished by injecting a suitable adhesive or embolizing material such as a cyanoacrylate, polyethylene glycol, hydrogel, fibrin glue through the delivery catheter lumen as the delivery catheter 12 is being pulled back through the tissue tract through which it was initially inserted. In other applications where the delivery catheter 12 remains indwelling, the backflow of fluid may be accomplished by a backflow barrier 22 (see FIG. 4) such as an annular rib or inflatable balloon formed on the shaft of the delivery catheter 12 near its distal end so as to block backflow of fluid around the catheter shaft or alternatively by causing the fluid to solidify or become gelatinous such that it can not backflow through the penetration tract. Such gelling or solidification of the injected fluid may be accomplished by subsequent injection or pre-mixing of the fluid with an oil, a gelatinous polymer carrier or reactant that will cause the desired thickening or solidification of the injected fluid.

Anti-Obstruction Apparatus for Maintaining Patency of Delivery Catheter

In some embodiments, especially those in which the delivery catheter 12 is allowed to remain indwelling for chronic delivery of substances or apparatus to the target site, the delivery catheter may incorporate anti-obstruction apparatus that will prevent cellular ingrowth or other matter from obstructing the lumen or outfow port(s) of the delivery catheter 12. Examples of such anti-blocking apparatus are shown in FIGS. 5-7.

In the embodiment of FIG. 5, the delivery catheter has a closed distal end 28 and a plurality of side outlet apertures 24. A solid stylet 26 is insertable through the lumen of the delivery catheter and the outer diameter of the stylet 26 is approximately the same as the inner diameter of the delivery catheter such that, when inserted, the stylet 26 will substantially close-off or block the side apertures 24 thereby preventing cellular ingrowth or other matter from entering the side apertures 24 or lumen of the delivery catheter. Thus, the stylet 26 may be inserted into the delivery catheter at times when no fluids or other substances are being infused, but may be removed at appropriate times to allow the desired infusions of fluids or other substances through the delivery catheter.

In an alternative variation of the embodiment shown in FIG. 5, the stylet 26 could have a lumen which extends longitudinally through the stylet to a closed distal end and side aperture(s) or slot(s) or other opening(s) could be formed in the stylet so as to be alignable with the side apertures 24 of the delivery catheter. In such embodiment, the stylet would be maintained in one position when it is desired to block the side apertures 24 to prevent cellular ingrowth or other matter from entering the side aperture's or lumen of the delivery catheter but may be rotated or otherwise moved to a second position wherein the aperture(s), slot(s) or other opening(s) of the style at 26 would become aligned with the side aperture's 24 of the delivery catheter is such that fluid may be injected through the lumen of the style that and outwardly through the side apertures of the delivery catheter 24. Thereafter, when the fluid injection has been completed, the stylet could be once again rotated or otherwise moved to the first position to once again close-off or block the side apertures 24 of the delivery catheter.

FIGS. 6a and 6b show another embodiment wherein the delivery catheter has a closed distal end 28 and a plurality of side outlet apertures 24. In this embodiment, an inflatable obturator 30 is disposed within the lumen of the delivery catheter. When the obturator 30 is inflated, as shown in FIG. 6a, it will close-off or block the side apertures 24 thereby preventing cellular ingrowth or other matter from entering the side apertures 24 or lumen of the delivery catheter. However, when the obturator 30 is deflated, as shown in FIG. 6b, fluids may be infused in the distal direction through the lumen of the delivery catheter and out of the side apertures 24.

In the embodiment of FIG. 7, a semi-permeable diffusion barrier 58 is mounted about the outer surface of the delivery catheter so as to cover the catheter's side apertures 24. This diffusion barrier 58 is in the nature of a balloon and is formed of material that permits the substances or fluids injected through the catheter to diffuse outwardly through the barrier 58, but also prevents cellular ingrowth or other matter from invading the interior of the barrier 58 and entering the side apertures 24 or lumen of the delivery catheter. The desired semi-permeability of the diffusion barrier 58 may be a function of the size of pores or openings in the barrier or balloon 24. Thus, polymer films having appropriately sized pores may be used to form the diffusion barrier 58. One polymer material that may be used in film form to create the diffusion barrier 58 is commercially available as Nutrapore™ from Anamed, Inc., 1 Technology Drive, Bldg. D-409, Irvine, Calif. 92618.

FIGS. 8a and 8b show another embodiment of a delivery catheter 12 having it opened distal end and a spring-mounted tip member 42 disposed within the distal end of the catheter 12. The tip member 42 has a fluid flow channel 44 that extends through the tip member 42 and opens through the side of the tip member 42, as shown. The tip member 42 is attached to the catheter 12 by way of a spring 40. The spring 40 is biased to a contracted position as shown in FIG. 8a, wherein the tip member 42 is drawn into the lumen of the catheter 12 such that the side opening of the fluid flow channel 44 is covered by the wall of the catheter 12 and cellular ingrowth or other matter is thereby prevented from entering the fluid flow channel 44 or lumen 32 of the delivery catheter 12. However, as shown in FIG. 8b, when fluid or some substances injected in the distal direction through the lumen 32 of the catheter 12, the pressure of the fluid or other substance will overcome the bias of the spring 40, causing the tip member 42 to advance to a second position whereby the side opening of the fluid flow channel 44 becomes unobstructed and the injected substance or fluid is permitted to flow outwardly through the fluid flow channel 44 and out of its side opening, into the surrounding tissue. Thereafter, when the substance or fluid is no longer being injected, the bias of the spring 40 will cause the tip member 42 to retract to its first position as shown in FIG. 8a.

In the embodiment shown in FIGS. 9a and 9b, there is provided a delivery catheter 12 that has an open distal end, a generally conical tip member 408 and a coil spring member 46 which attaches the tip member 48 to the distal end of the catheter 12. The coil spring member 46 is biased to a retracted position, as shown in FIG. 9a, wherein the convolutions of the coil spring member 46 are drawn into abutment with one another and with the respective ends of the catheter body 12 and tip member 48. In this manner the distal end of the catheter 12 is substantially closed, and cellular ingrowth or other matter is prevented from invading the lumen of the catheter 12. However, as shown in FIG. 9b, when a fluid or substance is injected through the lumen of the catheter 12 the pressure of the injected fluid or substance will overcome the bias of the coil spring member 46, thereby causing the tip member 46 to advance in the distal direction and the convolutions of the coil spring member 46 to separate such that spaces 46a will exist between the individual convolutions of the coil spring member 46. The injected substance or fluid will thus flow outwardly through the spaces 46a and into the surrounding tissue. After the injection of the substance or fluid has stopped, the bias of the coil spring member 46 will cause the tip member 48 to become retracted and the device will assume its closed configuration as shown in FIG. 9a.

Another way in which the patency of the lumen of the delivery catheter 12 may be maintained is by constant infusion and withdrawal of fluid therethrough. In this regard, fluid may be continually or periodically infused into a tissue pocket or reservoir at the distal end of the delivery catheter 12 and subsequently re-aspirated through the delivery catheter lumen. Alternatively, the delivery catheter 12 may have multiple lumens, one for infusion of fluid and one for withdraw of fluid, and a periodic or continual infusion and withdrawal of fluid may be performed to keep these lumens of the delivery catheter 12 open and unobstructed with cellular ingrowth, clots, debris or other matter.

Apparatus/Substances for Anchoring of Delivery Catheter

The delivery catheter 12 may incorporate mechanical hooks, screws, barbs or other anchoring members (not shown) that engage surrounding tissue and deter inadvertent migration or movement of the delivery catheter 12 after it has been implanted. Such anchoring members may be formed of bioabsorbable material and may be designed to break away, detach upon delivery of a pulse of energy or to be otherwise jettisoned when the delivery catheter 12 is purposefully removed from the body. In instances where the optional interactive member 52 comprises an energy emitter or electrode, such as a radiofrequency electrode, such interactive member 52 may be actuated after the delivery catheter 12 is in place for the purpose of fusing the catheter 12 to the surrounding tissue. Also, chemical glues, adhesives, or an ingrowth matrix such as a fabric (e.g., a woven material such as Dacron) into which surrounding tissue will grow, may be disposed on the delivery catheter 12 or introduced through the delivery catheter 12 after it is positioned, to deter inadvertent movement of the delivery catheter 12.

Other Surface Treatments of the Delivery Catheter

Apart from the above-described disposition of glues, adhesives or an ingrowth matrix on the surface of the delivery catheter 12 to facilitate its anchoring, there may additionally be other types of surface materials or surface treatments applied to the delivery catheter 12 for various other reasons. For example, the outer surface of at least the portion of the delivery catheter that becomes inserted into the patient's body may be coated or impregnated with and antibiotic or antimicrobial substance (e.g. provodine iodine, silver compounds, etc.) or other drugs or substances that affect the surrounding tissue in a desired way (e.g., a heparin coating that will reduce clot formation in areas adjacent to the catheter or within the blood vessels through which the catheter extends). One example of an anti-microbial coating that may be applied to the delivery catheter 12 is a proprietary material containing silver, carbon and platinum and used commercially under the name Oligon™ (Edwards Lifesciences Corporation, Irvine, Calif.). Examples of commercially available heparin coatings that may be used include heparin-benzalkonium chloride complex, heparin-TDMAC complex and other medical coatings available from STS Biopolymers, Inc. 336 Summit Point Dr., Henrietta, N.Y.

Apparatus for Creating Pocket into Which Substance or Apparatus is Introduced:

The delivery catheter 12 may optionally incorporate, or may be used in conjunction with, apparatus for creating a pocket (e.g., a void) within tissue located adjacent to the outflow aperture(s) 24 of the delivery catheter 12 such that substances infused through or apparatus introduced through the delivery catheter 12 will be received within that pocket. For example, an expandable cage may be deployable through or from the delivery catheter 12 to spread or separate the adjacent tissue, thereby creating the desired pocket. Or, the above-described interactive member 52 may comprise an energy emitting apparatus capable of creating a pocket adjacent thereto. In this regard, the interactive member 52 may comprise a radiofrequency electrode that, when actuated, will ablate the adjacent tissue thereby creating the desired pocket. Alternatively, the pocket creating apparatus may comprise a laser port through which ablative laser energy may pss into the adjacent tissue, or a nozzle through which a high pressure jet of fluid may be injected so as to sever or separate the adjacent tissue, thereby creating the pocket.

Variable Delivery Catheter Trajectory from Single Penetrator

Figure 13:
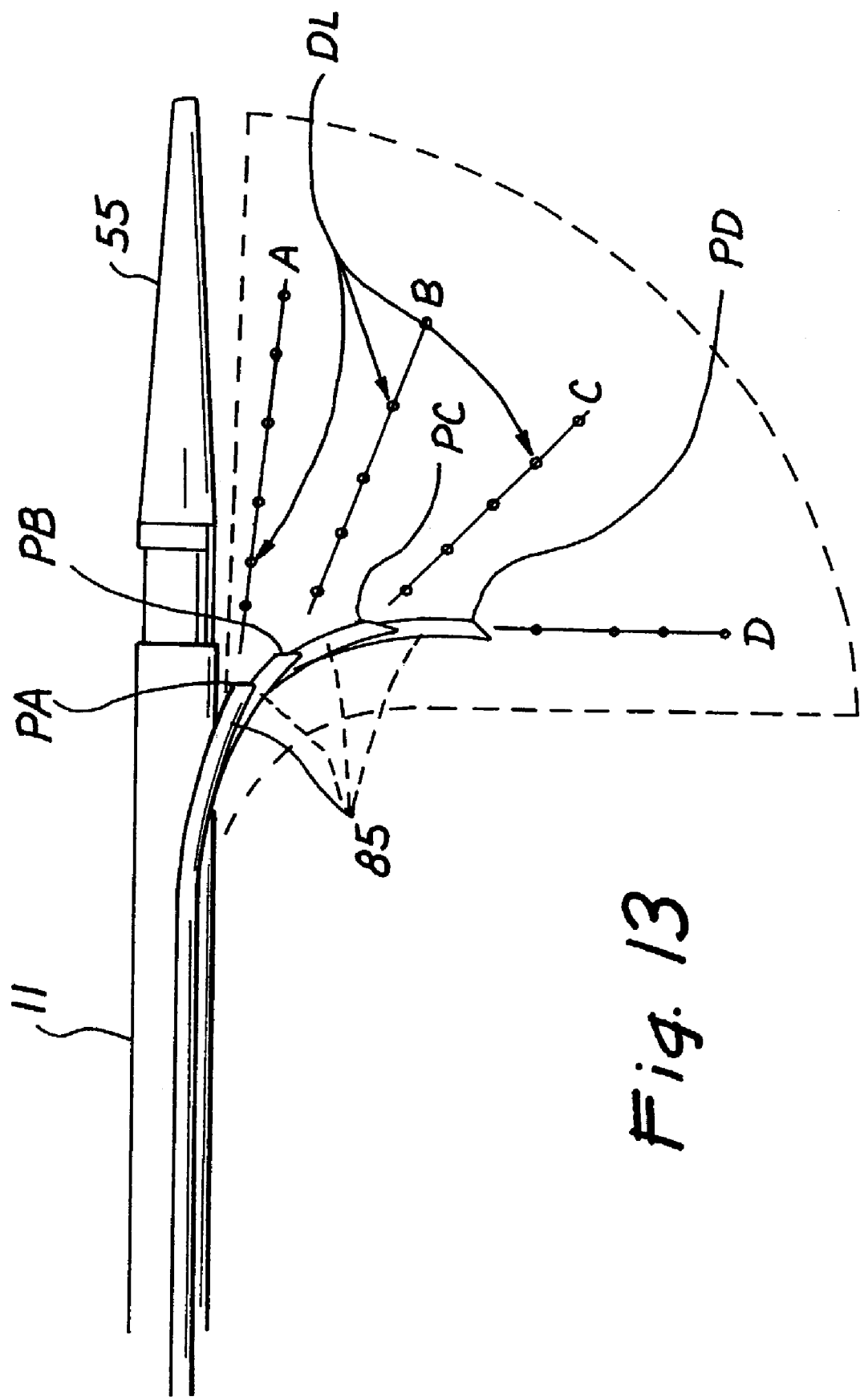

FIG. 13 shows that the vessel wall penetrator 85 may be of a pre-bent, curved configuration such that incremental advancement of the penetrator may cause its distal tip to be incrementally positioned at a series of different locates, such as point A (PA), point B (PB), point C (PC) and point D (PD) shown in FIG. 13. The delivery catheter 12 may then be advanced out of the penetrator at each of the points and drug or substances may be injected at periodic depot locations DL along the path of each advancement or retraction of the delivery catheter 12. In this manner, the drug or other substance may be deposited relatively uniformly over a generally wedge shaped region of tissue with only one penetration through the vessel wall.

B. Procedure for Transluminal Placement of a Delivery Catheter Within and Interstitial Target Site and Acute or Chronic Delivery of Substances or Apparatus to the Target Site:

FIG. 1 generally depicts a catheter system 10 of the above-described type being used to perform a procedure for transvenous placement of a delivery catheter 12 in an ischemic region of the patient's myocardium (i.e., the target site) so that a substance or apparatus may be acutely or chronically delivered directly into the target site.

Figure 11:
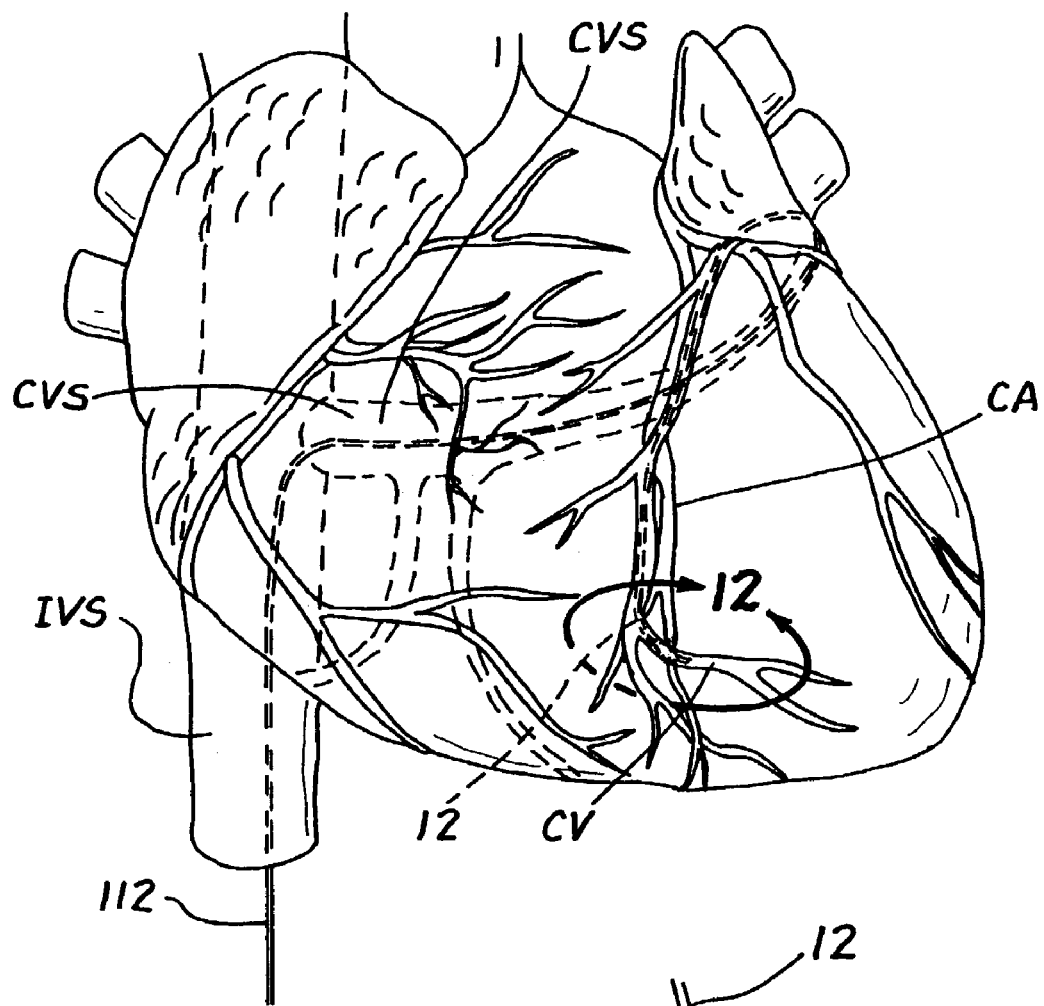

This procedure begins with the percutaneous insertion of the vessel wall penetrating catheter 11 into the patient's femoral vein and advancement of the vessel wall penetrating catheter 11 trough the inferior vena cava, through the right atrium, through the coronary venous sinus and into a coronary vein as shown in detail in FIG. 11. A vessel wall penetrator 85 is then advanced from the vessel wall penetrating catheter 11 and through the wall of the coronary vein in which the vessel wall penetrating catheter 11 is positioned. Thereafter, a delivery catheter 12 is advanced through the vessel wall penetrator 85 to the target location within the patient's myocardium.

In many applications, the vessel wall penetrating catheter 11 will be provided with or associated with guidance elements as described hereabove to guide the positioning, rotational orientation of the catheter 11 within the patient's body and/or the path, trajectory and extent of advancement of the penetrator 85. Typically, these guidance elements will be used to guide the longitudinal position and rotational orientation of the vessel wall penetrating catheter 11 before the penetrator 85 is advanced from the catheter 11. Thereafter, after the delivery catheter 12 has been advanced through the penetrator 85 to the target site, the penetrator 85 may be retracted into the vessel wall penetrating catheter 11 and the vessel wall penetrating catheter 11 may be withdrawn and removed, leaving only the delivery catheter 12 in place.

Optionally, as shown in FIG. 2c, an interactive member 52 such as an emitter, sensor, marker, electrode, etc. may be mounted on the delivery catheter 12. This interactive member 52 may be sensor (e.g., an electrode, optical sensor, chemical sensor, strain gage, flow meter, etc) that is connected to a receiver or instrumentation located outside the patient's body so as to provide information or analytical data regarding from the target site TS. Examples of the types of information or data that may be sensed and provided from the target site include ECG, contractility, force of contraction, pressure, local ECG amplitude, local protein levels, local antibody levels, $PO_2$, $pCO_2$, oxygen saturation, blood flow rate, pH, local lactate levels, etc.

Substances or apparatus may be introduced through the lumen of the delivery catheter 12 at desired time points or intervals. Also, separate sensor(s) or other separate apparatus may be delivered through the delivery catheter 12 so as to provide diagnostic information or other information regarding the physiological status of the myocardium in which the delivery catheter 12 is indwelling and/or the specific positioning of the distal end of the second catheter 12. After all of the desired sampling, diagnosis, delivery of substances and/or delivery of apparatus has been completed, the dosing catheter 12 may then be removed from the body of the patient. Some examples of tissue penetrating catheters 10 useable in this invention include those described in PCT International Patent Publications No. PCT/US99/07115 and PCT/US99/07112.

The delivery catheter 12 may comprise any suitable type of flexible catheter sized to pass through the lumen of the vessel wall penetrator 85 in the manner described here above. Examples of commercially available extrusion that may be used to form the delivery catheter 12 include a When the invention is used to deliver substances (e.g., drugs, therapeutic agents, biologicals, etc.) to ischemic site(s) within the myocardium, the types of substances that may be delivered include angiogenic factors (e.g. VEGF, FGF, EGF, PDGF or Hepatocyte Growth Factor ("HGF")), gene therapy compositions (e.g. a replication-deficient adenovirus vector containing a transgene which codes for an angiogenic protein or peptide), pro-angiogenic agents or combinations (e.g. an adenosine receptor agonist in combination with heparin), myocardial cells, myocytes, myoblasts, or other cardiac or systemic drugs such as antiarithmic agents, beta blockers, calcium channel antagonists, platelet glycoprotein (GP) IIb/IIIa inhibitors, etc.

In some applications, the invention may be used to treat neurdegenerative diseases such as Parkinson's Disease, Amilotrophic Lateral Sclerosis (Lou Gehrig's Disease), Alzheimer's Disease, etc.) By delivering to a target site within the brain or central nervous system a substance that delays the nerve cell degeneration or causes new nerve cells or new nerve cell connections to form, such substances including but not limited to glial cell line-derived neurotropic factor (GDNF), nerve growth factor, neuro-immunophilin ligand, poly ADP-Ribose polymerase, and combinations thereof.

In some applications of the invention, the delivery catheter 12 will be provided with small side apertures 24 and a closed distal end, or some other aperture or nozzle arrangement, that causes the substance to be expelled from the delivery catheter 12 in fine, high velocity jets or streams such that dissemination of the substance into the surrounding tissue will be enhanced. In some instances an interactive member 52 on the delivery catheter may be used emit energy or otherwise interact with the delivered substance to affect the substance in a desired way (e.g., to emit an iontophoretic field to drive the substance into adjacent tissue or to cause the distal tip of the delivery catheter 11 to become warm or to vibrate ultrasonically in a way that enhances the distribution or cell membrane permeation of the substance). Also, in some applications, a substance injected through the delivery catheter 12 may be mixed with or followed by a second substance which causes the first substance to solidify, gel, adhere or to become otherwise altered in a desired manner (e.g., in a way that affects the distribution, bioavailability, potency, duration of action or pharmacologic activity of the first substance. In this regard, a mixture of angiogenic factors (e.g., VegF and FGF) may be prepared in a liquid polymer matrix and injected in a bolus through the delivery catheter 12 into a myocardial target site. Thereafter, a second solution containing a catalyst that causes the polymer matrix to solidify to form a biodegradable solid may be injected as a second bolus through the delivery catheter. The mixture of the fist solution with the second solution within the target site will cause the fist solution to solidify in the form of a biodegradable solid or foam. This in situ solidification of the matrix will cause the injected angiogenic factors to remain within the target site for a longer period of time than if they had been injected and allowed to remain as an aqueous solution. Examples of materials that may be formed in situ in this application include those described in U.S. Pat. No. 6,139,574 (Vacanti).

The present invention allows for mapping or assessment of the site at which the delivery catheter 12 is positioned to confirm that the site is, or continues to be, suitable for the intended purpose. For example, a radio-labeled compound, radio-isotope or other traceable substance may be introduced through the delivery catheter and the rate at which the radio-labeled substance or isotope distributes away from the injection site may be measured by well known techniques. If the distribution away from the site is determined to be too rapid or too slow, the delivery catheter 12 may be repositioned before the desired therapeutic or diagnostic substance is injected. In chronic dosing applications wherein the delivery catheter 12 remains indwelling for days or months, this technique may be used to ensure that the delivery catheter 12 has not migrated or moved from the intended injection site, or that the site has not become excessively vascularized since delivery of the last dose. In some applications, it may be desirable for the delivery catheter 12 to have multiple lumens, such that the desired therapeutic or diagnostic substance or apparatus may be delivered through one lumen and a traceable substance useable for mapping or assessment of the target site may be delivered through another lumen.

It will be appreciated that the above-described examples of the application of the catheter system 10 may further be combined with some or all of the other optional elements of the catheter system 10 described here above, such as the high-pressure distribution nozzles, tissue-pocket-creating apparatus, sponges or other apparatus/substances afford to wait or affect the dissemination or distribution of the injected substance, anti-obstruction apparatus, apparatus/substances for a three of the delivery catheter, sensors or other apparatus for characterization of the targets i.e. or regions adjacent the delivery catheter, etc.

C. Method for Intravenous Retroperfusion

Figure 12:
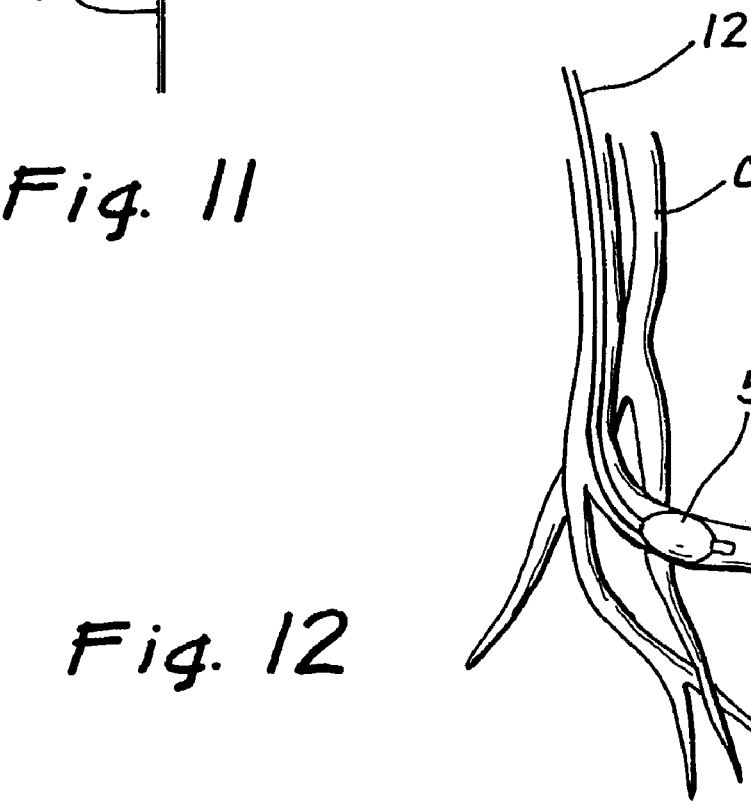

The present invention further includes a method wherein a retrovenous delivery catheter 112, a shown in FIGS. 11 and 12, is used to deliver a substance into a vein while temporarily obstructing the vein, thereby allowing the substance to enter a target ste by undergoing retrograde flow through the venous vasculature to a capillary bed at the target site. The retrovenous delivery catheter 112 generally comprises a flexible tubular catheter described hereabove of the above-described type may be inserted into a selected vein (e.g., a coronary vein) and used acutely or chronically to deliver substances to a particular target site by retroperfusion of the substance through the vein, to a capillary bed located within the target site. An example of this embodiment of the invention is shown in FIGS. 11 and 12. As shown, the retrovenous catheter 112 has a distal end opening and an inflatable occlusion balloon 50 formed a spaced distance proximal to the distal end opening. The catheter 112 is inserted into the venous vasculature and advanced into a specific vein such as a coronary vein located near an area of ischemic myocardium, as shown in FIGS. 11 and 12. Before a desired substance is delivered through the catheter 112, the occlusion balloon 50 is inflated so as to occlude the vein and prevent venous blood from flowing through the vein in the normal direction of venous blood flow. The desired substance (e.g., a drug or biological) is then injected through the catheter 112 and out of its distal end opening into the vein. Because the vein is occluded by the balloon, the injected substance will flow in retrograde fashion through the vein and to the capillary bed within the ischemic region of the myocardium. The balloon may remain inflated for a desired period of time to allow the drug or substance to be effectively absorbed by the tissues adjacent to that capillary bed. Thereafter, the balloon is deflated, allowing normal venous flow through the vein. The catheter 112 may be removed after a single dose is delivered or it may remain indwelling for a period of time (e.g., hours, days, weeks or months) to permit repeated doses to be delivered by repeating the foregoing injection procedure. Any or all of the attributes and options described above with respect to the extravascular delivery catheter 12 may also be incorporated into this retrovenous delivery catheter 112, to the extent feasible and not adverse to the intended function of this retrovenous delivery catheter as described herein.

Although exemplary embodiments of the invention have been shown and described, many changes, modifications and substitutions may be made by those having ordinary skill in the art without necessarily departing from the spirit and scope of this invention. Specifically, elements or attributes described in connection with one embodiment may also be used in connection with another embodiment provided that the inclusion or use of such element or attribute would not render the embodiment in which it is incorporated unuseable or otherwise undesirable for an intended application. Accordingly, all such additions, deletions, modifications and variations to the above-described embodiments are to be included within the scope of the following claims.

What is claimed is:

1. A catheter device for delivering a substance or apparatus to a target site located within the body of a human or veterinary patient, said device comprising:
    an elongate catheter body having a distal end, said catheter body being positionable in a blood vessel lumen;
    a hollow penetrator member positioned within the catheter body and advanceable therefrom;
    at least one imageable marker that indicates the rotational orientation of the catheter body within the blood vessel lumen, said marker being useable to enable an operator to rotationally orient the catheter body relative to the target site such that subsequent advancement of the penetrator will cause the penetrator to move to a first location that is within or near the target site; and,
    a delivery catheter that is advanceable through the hollow penetrator to the target site, the substance or apparatus being deliverable to the target site through said delivery catheter.

2. A device according to claim 1 wherein the said at least one marker comprises a radiopaque marker.

3. A device according to claim 1 wherein said at least one marker is positioned and configured to mark the location of the lumen.

4. A device according to claim 1 wherein said at least one marker is positioned and configured to mark the location of the lumen adjacent to an aperture through which the hollow penetrator exits the catheter body.

5. A device according to claim 1 further comprising a guidewire lumen.

6. A device according to claim 1 further comprising a distal tip member on the distal end of the catheter body.

7. A device according to claim 6 wherein the distal tip member is formed of soft, flexible material.

8. A catheter device according to claim 1 further comprising an imaging apparatus on the catheter body, said imaging apparatus being useable to image the at least one imageable marker, thereby providing an image to enable the operator to position and rotationally orient the catheter body within the blood vessel lumen such that subsequent advancement of the penetrator member will cause the penetrator member to enter the target site.

9. A system comprising a catheter device according to claim 1 further in combination with an imaging apparatus that is not located on the catheter body, said said imaging apparatus being useable to image the at least one imageable marker, thereby providing an image to enable the operator to position and rotationally orient the catheter body within the blood vessel lumen such that subsequent advancement of the penetrator member will cause the penetrator member to enter the target site.

10. A system according to claim 9 wherein the imaging device comprises a fluoroscope.

11. A system comprising a catheter device according to claim 1 further in combination with a delivery catheter that is advanceable through the hollow penetrator member of the catheter device to the target site, the substance being deliverable through the delivery catheter.

12. A system according to claim 11 wherein the catheter device is removable leaving the delivery catheter in position within the patient's body.

13. A system according to claim 12 wherein the delivery catheter has a lumen and an outflow opening and wherein the system further comprises a matter blocking member that substantially deters unwanted matter from entering the outflow opening.

14. A system according to claim 13 wherein the matter blocking member comprises a selectively permeable barrier that allows a substance to be infused in the distal direction through the outflow opening and to the target location but prevents cellular ingrowth and other matter from entering the lumen of the delivery catheter through said outflow opening.

15. A system according to claim 14 wherein the selectively permeable barrier is a balloon attached to the delivery catheter such that a substance infused through the lumen of the delivery catheter will collect within the balloon and subsequently diffuse outwardly through the balloon.

16. A system according to claim 14 wherein the matter blocking member comprises a stylet that is insertable into the lumen of the delivery catheter to block the entry of matter into the lumen of the delivery catheter lumen.

17. A system according to claim 16 wherein the stylet is removable from the lumen of the delivery catheter to permit delivery of a substance or apparatus through the delivery catheter.

18. A system according to claim 11 wherein the delivery catheter comprises:
   a first tube having a lumen and a sidewall in which an outflow aperture is formed; and,
   a second tube rotatably disposed in a coaxial position within the first tube, said second tube having a lumen, a closed distal end and a sidewall in which an opening is formed;
   the second tube being rotatably moveable between i) a blocking position wherein the side wall of the second tube substantially blocks the outflow aperture of the first tube to prevent cellular ingrowth and other matter from entering the lumen of the second tube and ii) an infusion position wherein the opening of the second tube is aligned with the outflow opening of the first tube such that a substance that is injected into the lumen of the second tube will flow through the opening of the second tube and through the outflow opening of the first tube.

19. A system according to claim 18 wherein a plurality of outflow apertures are formed in the sidewall of the first tube.

20. A system according to claim 11 wherein the delivery catheter comprises:
   a tube having a lumen and a sidewall in which an outflow aperture is formed; and,
   an obturator member disposed at least partially within the lumen of the tube, said obturator member being alternately disposable in i) a blocking position wherein the obturator substantially blocks the outflow aperture of the tube to prevent cellular ingrowth and other matter from entering the lumen of the tube and ii) an infusion position wherein the obturator does not substantially block the outflow apertures such that fluid may be injected through the lumen of the tube and out of the outflow aperture.

21. A system according to claim 20 wherein a plurality of outflow apertures are formed in the sidewall of the tube.

22. A system according to claim 20 wherein the obturator member is an inflatable balloon that assumes said blocking position when inflated and said infusion position when deflated.

23. A system according to claim 11 wherein the delivery catheter comprises an infusion lumen, a return lumen, an outflow aperture through which an infused substance may flow out of the infusion lumen and a flow diverter, said flow diverter that is alternately deployable in i) an infusion position whereby the substance infused through the infusion lumen will flow out of the outflow aperture and ii) a recirculation position whereby fluid infused through the infusion lumen will be recirculated back through the return lumen.

24. A system according to claim 11 wherein the delivery catheter comprises a pressure increasing outflow opening configured to cause an increase the pressure of fluids that are injected through the delivery catheter lumen and out of said pressure increasing outflow opening.

25. A system according to claim 24 wherein said pressure increasing outflow opening is formed in the side wall of the delivery catheter.

26. A system according to claim 25 wherein a plurality of pressure increasing outflow openings are formed in the side wall of the delivery catheter.

27. A system according to claim 1 wherein the delivery catheter further comprises an anchoring member for anchoring the catheter in a substantially fixed position within the patient's body.

28. A system according to claim 27 wherein the anchoring member is selected from the group of anchoring members consisting of:
   a hook;
   a barb;
   a permeable surface into which tissue may grow;
   an adhesive; and,
   combinations thereof.

29. A system according to claim 1 wherein the delivery catheter further comprises a backflow deterrent member for blocking backflow of a substance that has been injected through the delivery catheter.

30. A system according to claim 29 wherein said backflow deterrent member comprises a backflow barrier rib formed on the delivery catheter.

31. A system according to claim 30 wherein said backflow barrier comprises an inflatable balloon on the delivery catheter.

32. A system according to claim 30 wherein said backflow barrier comprises a raised projection formed on the exterior of the delivery catheter.

33. A system according to claim 32 wherein the raised projection comprises an annular rib formed about the outer surface of the delivery catheter.

34. A system according to claim 30 wherein the backflow deterrent member comprises a sealant that is implanted prior to or concurrently with removal of the delivery catheter so as to prevent the injected substance from backflowing through the tract from which the delivery catheter is removed.

35. A system according to claim 34 wherein the sealant comprises a quantity of a flowable sealant injected into the tract upon removal of the delivery catheter.

36. A system according to claim 34 wherein the sealant comprises a detachable sealing member.

37. A system according to claim 36 wherein the detachable sealing member is formed of biodegradable material.

38. A system according to claim 36 wherein the detachable sealing member comprises a collagen sponge.

39. A system according to claim 36 wherein the detachable sealing member comprises a hydrogel sponge.

40. A system according to claim 1 wherein at least a portion of the delivery catheter is coated with an adhesive.

41. A system according to claim 1 wherein an anti-microbial substance is disposed on at least a portion of the delivery catheter.

42. A system according to claim 1 wherein an anti-coagulant substance is disposed on at least a portion of the delivery catheter.

43. A system according to claim 1 further comprising apparatus for creating a pocket within tissue adjacent to the delivery catheter such that when a substance or apparatus is introduced through the delivery catheter it will be received within said pocket.

44. A system according to claim 43 wherein the apparatus for creating a pocket comprises an energy emitting member that emits energy into adjacent tissue to create said pocket.

45. A system according to claim 44 wherein the energy emitting apparatus comprises a radiofrequency electrode.

46. A system according to claim 45 wherein the energy emitting apparatus comprises a laser.

47. A system according to claim 44 wherein the apparatus for creating a pocket comprises a nozzle through which a stream of fluid may be injected to create the pocket in adjacent tissue.

48. A system according to claim 44 wherein the apparatus for creating a pocket comprises an expandable cage which, when expanded, creates said pocket.

49. A system according to claim 1 further in combination with an infusion apparatus for infusing a substance through the delivery catheter.

50. A system according to claim 49 wherein said infusion apparatus comprises a syringe.

51. A system according to claim 49 wherein said infusion apparatus comprises a pump.

52. A system according to claim 49 wherein said infusion apparatus is a reservoir positioned for gravity drainage of the substance through the delivery catheter.

53. A system according to claim 49 wherein said infusion apparatus further comprises a quantity of a substance for infusion through the delivery catheter.

54. A system according to claim 53 wherein the substance comprises a drug.

55. A system according to claim 54 wherein the drug is selected from the group consisting of: thrombolytics, platelet inhibitors, anti-restenotic agents, beta adrenergic blockers, ion channel antagonists, positive or negative ionotropic agents, anti-arrhythmics and combinations thereof.

56. A system according to claim 53 wherein the substance comprises a protein.

57. A system according to claim 53 wherein the substance comprises an angiogenic substance.

58. A system according to claim 57 wherein the angiogenic substance is selected from the group consisting of vascular endothelial growth factor (VEGF), fibroblast growth factors (FGF), epidermal growth factor (EGF), platelet-derived growth factor (PDGF), hepatocyte growth factor (HGF) or scatter factor, heparin combined with an adenosine receptor agonist, and combinations thereof.

59. A system according to claim 53 wherein the substance comprises cells.

60. A system according to claim 59 wherein the substance comprises progenator cells for a type of cell that is desired to be formed at the target site.

61. A system according to claim 59 wherein said substance comprises myoblasts to form cardiac muscle cells.

62. A system according to claim 59 wherein said cells are selected from the group consisting of stem cells, progenator cells, myoblasts, myocytes, secretory cells, pancreatic islet cells, dopamine secreting cells, endothelial cells, hepatocytes, cloned cells, cells grown in cell culture, genetically modified cells, and combinations thereof.

63. A system according to claim 53 wherein the substance is a gene.

64. A system according to claim 53 wherein the substance comprises a gene and a vector for facilitating entry of the gene into locations within cells at which the gene will have a desired effect on the cells.

65. A system according to claim 64 wherein the vector comprises a virus.

\* \* \* \* \*